United States Patent
Kim et al.

(10) Patent No.: US 10,941,136 B2
(45) Date of Patent: Mar. 9, 2021

(54) QUINAZOLINE DERIVATIVE OR ITS SALT AND PHARMACEUTICAL COMPOSITION COMPRISING THE SAME

(71) Applicant: YUHAN CORPORATION, Seoul (KR)

(72) Inventors: Young-Hwan Kim, Hwaseong-si (KR); Tae-Dong Han, Yongin-si (KR); Dong-Hoon Kim, Suwon-si (KR); Eun-Hye Jung, Yongin-si (KR); Su-Bin Choi, Yongin-si (KR); Eui-Chul Lee, Yongin-si (KR); Won-Ee Chong, Hwaseong-si (KR); Jin-Hwi Park, Hwaseong-si (KR); Jun-Chul Park, Yongin-si (KR); Ho-Woong Kang, Yongin-si (KR); Ji-Yeong Gal, Yongin-si (KR); Chan-Sun Park, Hwaseong-si (KR); Jong-Gyun Kim, Anyang-si (KR); Su-Youn Nam, Seoul (KR)

(73) Assignee: YUHAN CORPORATION, Seoul (KR)

(*) Notice: Subject to any disclaimer, the term of this patent is extended or adjusted under 35 U.S.C. 154(b) by 332 days.

(21) Appl. No.: 16/096,712

(22) PCT Filed: Apr. 26, 2017

(86) PCT No.: PCT/KR2017/004424
§ 371 (c)(1),
(2) Date: Oct. 26, 2018

(87) PCT Pub. No.: WO2017/188720
PCT Pub. Date: Nov. 2, 2017

(65) Prior Publication Data
US 2020/0325120 A1  Oct. 15, 2020

(30) Foreign Application Priority Data

Apr. 29, 2016 (KR) .................. 10-2016-0053033

(51) Int. Cl.
| C07D 239/91 | (2006.01) |
| C07D 403/14 | (2006.01) |
| C07D 217/24 | (2006.01) |
| A61K 31/51 | (2006.01) |
| A61K 31/506 | (2006.01) |
| C07D 403/12 | (2006.01) |

(52) U.S. Cl.
CPC .......... C07D 403/14 (2013.01); A61K 31/506 (2013.01); A61K 31/51 (2013.01); C07D 217/24 (2013.01); C07D 239/91 (2013.01); C07D 403/12 (2013.01)

(58) Field of Classification Search
CPC .... C07D 239/72; C07D 403/04; A61K 31/51; A61K 31/506

USPC .................. 544/283, 296; 514/266.2, 266.3
See application file for complete search history.

(56) References Cited

U.S. PATENT DOCUMENTS

| 8,440,651 | B2 | 5/2013 | Castanedo et al. |
| 8,563,540 | B2 | 10/2013 | Castanedo et al. |
| 8,569,296 | B2 | 10/2013 | Liang |
| 8,969,363 | B2 | 3/2015 | Castro et al. |
| 9,150,579 | B2 | 10/2015 | Vakkalanka et al. |
| 9,475,818 | B2 | 10/2016 | Vakkalanka et al. |
| 2011/0207713 | A1 | 8/2011 | Castanedo et al. |
| 2012/0202805 | A1 | 8/2012 | Liang |
| 2013/0029982 | A1* | 1/2013 | Castro .................. C07D 495/04 514/233.2 |
| 2013/0225557 | A1 | 8/2013 | Castanedo et al. |
| 2014/0011819 | A1 | 1/2014 | Vakkalanka et al. |
| 2014/0051699 | A1 | 2/2014 | Liang |
| 2015/0126506 | A1 | 5/2015 | Castro et al. |
| 2015/0361083 | A1 | 12/2015 | Vakkalanka et al. |
| 2017/0020881 | A1 | 1/2017 | Vakkalanka et al. |
| 2020/0325120 | A1* | 10/2020 | Kim ..................... C07D 239/91 |

FOREIGN PATENT DOCUMENTS

WO   2015/168079 A1   11/2015

OTHER PUBLICATIONS

Ali et al., "Inactivation of the PI3K p110δ breaks regulatory T cell-mediated immune tolerance to cancer", Nature, vol. 510, No. 7505, pp. 407-411, (2014).
Bader et al., "Oncogenic PI3K Deregulates Transcription and Translation", Nature Reviews: Cancer, vol. 5, pp. 921-929, (2005).
Barberis et al., "Targeting phosphoinositide 3-kinase γ to fight inflammation and more", Thromb Haemost, vol. 99, pp. 279-285, (2008).
Ji et al., "Inactivation of PI3Kγ and PI3Kδ distorts T-cell development and causes multiple organ inflammation", Blood, vol. 110, pp. 2940-2947, (2007).
Stephens et al., "The Gβγ Sensitivity of a PI3K Is Dependent upon a Tightly Associated Adaptor, p101", Cell, vol. 89, pp. 105-114, (1997).
Ward et al., "Isoform-specific phosphoinositide 3-kinase inhibitors as therapeutic agents", Current Opinion in Pharmacology, vol. 3, pp. 426-434, (2003).
Webb et al., "Cutting Edge: T Cell Development Requires the Combined Activities of the p110γ and p110δ Catalytic Isoforms of Phosphatidylinositol 3-Kinase", The Journal of Immunology, vol. 175, pp. 2783-2787, (2005).

* cited by examiner

Primary Examiner — Venkataraman Balasubramanian
(74) Attorney, Agent, or Firm — Vorys, Sater, Seymour & Pease LLP; Mih Suhn Koh

(57) ABSTRACT

The present invention provides a quinazoline derivative or its pharmaceutically acceptable salt, a process for the preparation thereof, a pharmaceutical composition comprising the same and a use thereof. The quinazoline derivative or its pharmaceutically acceptable salt has a selective inhibitory activity against the phosphatidylinositol 3-kinase delta subunit, and therefore can be usefully applied for preventing or treating cancer, along with avoiding side effects such as lymphopenia-associated inflammatory responses.

13 Claims, 1 Drawing Sheet

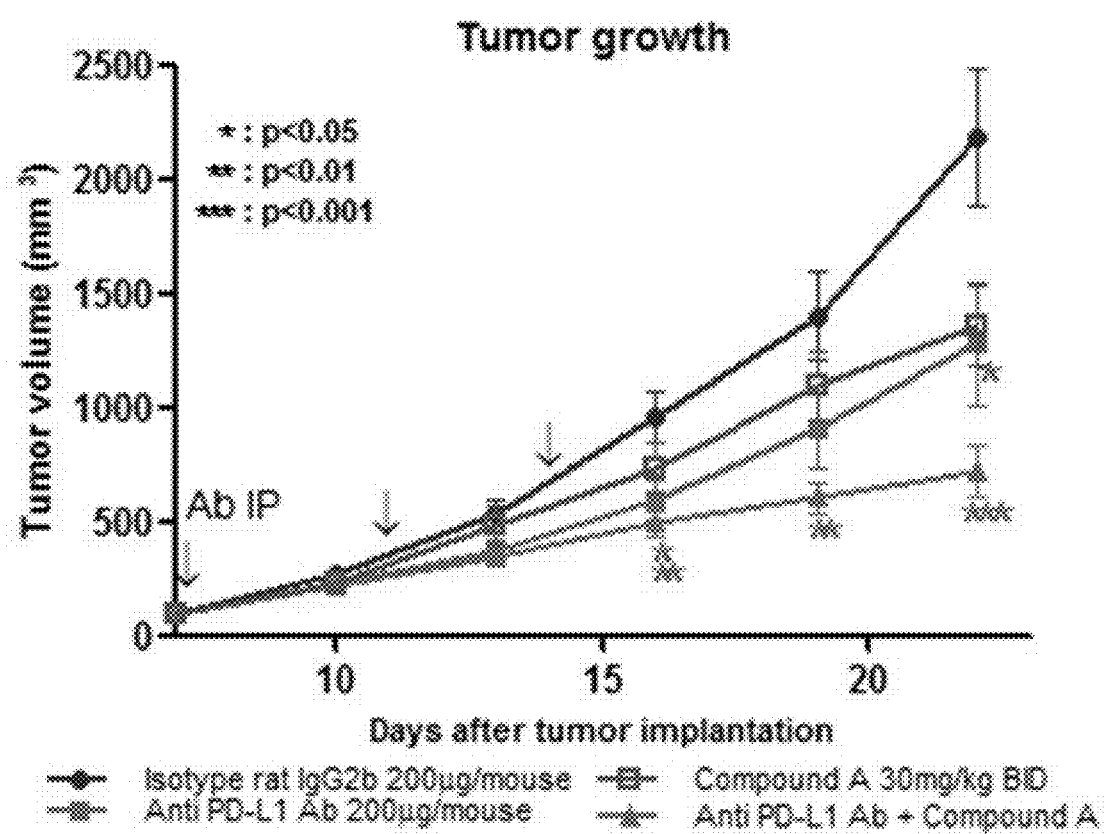

QUINAZOLINE DERIVATIVE OR ITS SALT AND PHARMACEUTICAL COMPOSITION COMPRISING THE SAME

TECHNICAL FIELD

The present invention relates to a quinazoline derivative or its pharmaceutically acceptable salt having a selective inhibitory activity against the phosphatidylinositol 3-kinase delta subunit, a process for the preparation thereof, a pharmaceutical composition comprising the same and a use thereof.

BACKGROUND ART

Phosphatidylinositol 3-kinase (PI3K), a lipid kinase which phosphorylates the lipid at the 3-hydroxy residue of the inositol ring, is known to play a critical role in proliferation, survival, motility and so on of cells. Class I PI3Ks (PI3Kα, PI3Kβ, PI3Kδ, and PI3Kγ) are activated by receptor tyrosine kinases or GPCR (G-protein coupled receptor) to produce PIP3 (phosphatidylinositol 3,4,5-triphosphate), thereby activating the Akt. It has been known that the activated Akt phosphorylates TSC2, GSK3β, MDM2, FOXO, BAD and so on, thereby controlling cellular proliferation or survival, angiogenesis, etc. (Nature Rev. Cancer, 5, 921-929 (2005)).

Class I PI3Ks are a heterodimer consisting of a p110 catalytic subunit and a regulatory subunit, and the family is further divided into Class IA and Class IB enzymes on the basis of the regulatory partners and the regulatory mechanisms. Class IA enzymes consist of three catalytic subunits (p110α, p110β and p110δ), which dimerize with five regulatory subunits (p85α, p55α, p50α, p85β and p55γ), where all catalytic subunits are able to interact with all regulatory subunits to form various heterodimers. Class IA PI3Ks are generally activated in response to growth factor stimulation of receptor tyrosine kinases via interaction of the regulatory subunit SH2 domain with specific phospho-tyrosine residues of the activated receptor or adapter proteins, such as IRS-1. Both p110α and p110β are expressed in all cell types, whereas p110δ expression is more restricted to inflammatory cells including leukocytes and some epithelial cells. The only class IB enzyme consists of a p120γ catalytic subunit (also commonly referred to as 'p110γ'), which interacts with a p101 regulatory subunit (Cell, Vol. 89, 105-114 (1997)). In addition, it has been reported that the Class IB enzyme is activated by G-protein-coupled receptor systems (GPCRs) and expressed mainly in inflammatory cells, including leukocytes and macrophages, and cardiomyocytes (Curr. Opin. Pharmacol. 3(4), 426-434 (2003); Thromb Haemost 99: 279-285 (2008)).

The PI3K/AKT/mTOR pathway is important for the formation and development of cancer, and mutations in the PIK3CA gene expressing p110α, along with PTEN, are frequently observed in cancer. Accordingly, PI3Kα and PI3Kβ inhibitors or non-specific class I inhibitors have been developed as a therapeutic agent for carcinomas overexpressing a specific subunit of PI3Ks. Although said inhibitors initially appeared to show some efficacy, it has been revealed to have limited therapeutic effects due to dose-related side effects and resistant mechanisms that activate alternative signals.

PI3K inhibitors can attack cancer as an anticancer agent, through activating the anti-tumor immune responses. This has been suggested by studies in which the function of the PI3Kδ subunit was genetically inhibited through transgenic mice or in which a PI3Kδ subunit-specific inhibitor was administered to mice (Nature 2014, 510: 407-411). Suppression of the PI3Kδ subunit function in the mouse models of lung cancer, breast cancer and pancreatic cancer inhibited the function of regulatory T cells (Tregs) as well as the migration of Tregs to tumors. It has been demonstrated that suppression of the PI3Kδ subunit in animal models inhibits the regulatory T cells, thereby resulting in an anti-tumor immune environment that can inhibit cancer proliferation by host immunity. Therefore, it has been established that the method for specifically inhibiting the PI3Kδ subunit can be a mechanism of an immunological anticancer agent which induces immunity against cancer.

In order to identify the role of PI3Kδ and PI3Kγ, which are important subunits in the function of immune cells, studies have been conducted on mouse models lacking both genes (Blood, 2007, 110:2940-2947). According to the study, knock-out mice lacking both subunits display severe impairment of thymocyte development in the thymus, which leads to lymphopenia-associated inflammatory responses. And also, the other study has also reported that mice deficient in both PI3Kδ and PI3Kγ subunits have a profound block in T cell development (J. immunol., 2005, 175:2783-2787). Therefore, considering that normal T cell differentiation is important for inflammatory response as well as for anti-cancer immunity, it is expected that selective inhibition against only the PI3Kδ subunit (i.e., not inhibition against both PI3Kδ and PI3Kγ subunits) is a safer approach in terms of immune side effects.

DISCLOSURE

Technical Problem

The present inventors has found that a certain quinazoline derivative or its pharmaceutically acceptable salt has a selective inhibitory activity against the PI3Kδ subunit, and therefore can be usefully applied for preventing or treating cancer, along with avoiding side effects such as lymphopenia-associated inflammatory responses.

Therefore, the present invention provides the above quinazoline derivative or its pharmaceutically acceptable salt, a process for the preparation thereof, a pharmaceutical composition comprising the same, and a use thereof.

Technical Solution

According to an aspect of the present invention, there is provided a quinazoline-containing fused ring compound and its pharmaceutically acceptable salt.

According to another aspect of the present invention, there is provided a process for preparing said quinazoline-containing fused ring compound and its pharmaceutically acceptable salt.

According to still another aspect of the present invention, there is provided a pharmaceutical composition comprising said quinazoline-containing fused ring compound or its pharmaceutically acceptable salt as an active ingredient.

According to still another aspect of the present invention, there is provided a therapeutic method comprising administering said quinazoline-containing fused ring compound or its pharmaceutically acceptable salt.

According to still another aspect of the present invention, there is provided a use of said quinazoline-containing fused ring compound or its pharmaceutically acceptable salt for the manufacture of a medicament for preventing or treating cancer.

Advantageous Effects

The compound of the present invention, i.e., the quinazoline-containing fused ring compound or its pharmaceutically acceptable salt has a selective inhibitory activity against the PI3Kδ subunit, and therefore can be usefully applied for preventing or treating cancer, along with avoiding side effects such as lymphopenia-associated inflammatory responses. And also, co-administration of the compound or its pharmaceutically acceptable salt of the present invention with an immune-checkpoint inhibitor, e.g., a negative regulating antibody of T-lymphocyte activation (for example, anti-PDL1 antibodies) can exhibit synergistic anticancer activity.

DESCRIPTION OF DRAWINGS

The FIGURE shows the results obtained by evaluating the anti-tumor efficacies of the compound according to the present invention and/or the immune-checkpoint inhibitor in murine syngeneic tumor model.

BEST MODE FOR CARRYING OUT THE INVENTION

As used herein, the term "alkyl" refers to a straight or branched aliphatic hydrocarbon radical. For example, the $C_{1-6}$ alkyl means a straight or branched aliphatic hydrocarbon having 1 to 6 carbon atoms, such as methyl, ethyl, propyl, n-butyl, n-pentyl, n-hexyl, isopropyl, isobutyl, sec-butyl, tert-butyl, neopentyl, and isopentyl.

The term "hydroxy" refers to the '—OH' group. The term "alkoxy" refers to a radical formed by substituting the hydrogen atom in the hydroxyl group with an alkyl. For example, the $C_1$-$C_6$ alkoxy group includes methoxy, ethoxy, propoxy, n-butoxy, n-pentyloxy, isopropoxy, sec-butoxy, tert-butoxy, neopentyloxy, and isopentyloxy.

The term "halogen" refers to the fluoro, bromo, chloro, or iodo group.

The term "amino" refers to the '—NH$_2$' group. The term "alkylamino" refers to an amino group substituted with mono- or di-alkyl. For example, the $C_{1-6}$ alkylamino group includes an amino group substituted with mono- or di-$C_{1-6}$ alkyl group.

The term "alkylthio" refers to the '—SR' group, in which R is an alkyl. The term "cyano" refers to the '—CN'.

The present invention provides a compound or its pharmaceutically acceptable salt having a selective inhibitory activity against the PI3Kδ subunit, i.e., a compound of Formula 1 or its pharmaceutically acceptable salt:

<Formula 1>

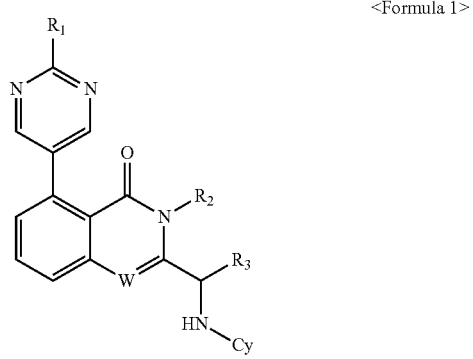

wherein,

W is N or CH, $R_1$ is hydrogen; a $C_{1-6}$ alkyl group; a $C_{3-8}$ cycloalkyl group; a $C_{1-6}$ alkoxy group; an amino group; a $C_{1-6}$ alkylamino group; a $C_{1-6}$ alkylthio group; or a halogen group, $R_2$ is hydrogen; a $C_{1-6}$ alkyl group; a $C_{3-8}$ cycloalkyl group; a $C_{3-8}$ heterocycloalkyl group; a substituted or unsubstituted aryl group; or a substituted or unsubstituted heteroaryl group, $R_3$ is hydrogen; a $C_{1-6}$ alkyl group; a $C_{3-8}$ cycloalkyl group; or a $C_{3-8}$ heterocycloalkyl group, and Cy is a group of the following Formula A or B, where * in Formulas A and B represents the position attached to the compound of Formula 1

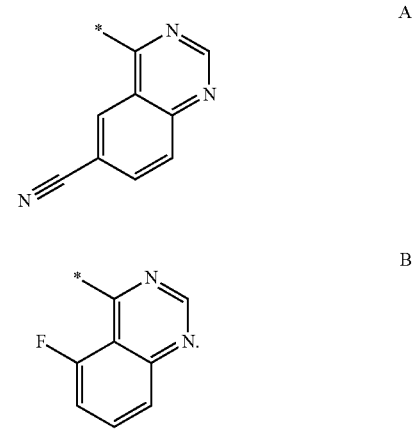

As used herein, the expression "having a selective inhibitory activity against the PI3Kδ subunit" refers to 'having significantly higher inhibitory activity against the PI3Kδ subunit, among the PI3Kα, PI3Kβ, PI3Kδ, and PI3Kγ subunits'. In an embodiment, the expression "significantly higher inhibitory activity against the PI3Kδ subunit" means that the IC$_{50}$ against the PI3Kδ subunit obtained from an in vitro enzyme assay is at least 3 times lower than the IC$_{50}$ against the PI3Kγ subunit obtained therefrom. In another embodiment, the expression "significantly higher inhibitory activity against the PI3Kδ subunit" means that the IC$_{50}$ against the PI3Kδ subunit obtained from an in vitro enzyme assay is at least 25 times lower than the IC$_{50}$ against the PI3Kα subunit obtained therefrom, at least 200 times lower than the IC$_{50}$ against the PI3Kβ subunit obtained therefrom, and at least 3 times lower than the IC$_{50}$ against the PI3Kγ subunit obtained therefrom.

In the compound of Formula 1 or its pharmaceutically acceptable salt, $R_2$ may be a $C_{3-8}$ cycloalkyl group or a phenyl group optionally substituted with halogen.

And also, in the compound of Formula 1 or its pharmaceutically acceptable salt, $R_3$ may be a $C_{1-6}$ alkyl group or a $C_{3-8}$ cycloalkyl group.

In an embodiment of the present invention, there is provided a compound of Formula 1a or its pharmaceutically acceptable salt wherein W is N:

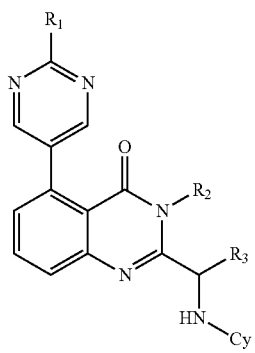

<Formula 1a> wherein, $R_1$, $R_2$, $R_3$ and Cy are the same as defined in the above.

In the compound of Formula 1a or its pharmaceutically acceptable salt, $R_1$ may be hydrogen; a $C_{1-6}$ alkyl group; a $C_{1-6}$ alkoxy group; an amino group; a $C_{1-6}$ alkylamino group; a $C_{1-6}$ alkylthio group; or a halogen group. Preferably, $R_1$ may be hydrogen; a $C_{1-6}$ alkyl group; a $C_{1-6}$ alkoxy group; an amino group; a $C_{1-6}$ alkylthio group; or a halogen group. More preferably, $R_1$ may be hydrogen; a $C_{1-6}$ alkyl group; a $C_{1-6}$ alkoxy group; or an amino group. Particularly preferably, $R_1$ may be $C_{1-6}$ alkoxy group or an amino group. In the compound of Formula 1a or its pharmaceutically acceptable salt, $R_2$ may be a $C_{3-8}$ cycloalkyl group or a phenyl group. Preferably, $R_2$ may be a phenyl group. In the compound of Formula 1a or its pharmaceutically acceptable salt, $R_3$ may be a $C_{1-6}$ alkyl group or a $C_{3-8}$ cycloalkyl group.

In an embodiment of the compound of Formula 1a or its pharmaceutically acceptable salt, $R_1$ is hydrogen; a $C_{1-6}$ alkyl group; a $C_{1-6}$ alkoxy group; an amino group; a $C_{1-6}$ alkylamino group; a $C_{1-6}$ alkylthio group; or a halogen group, $R_2$ is a $C_{3-8}$ cycloalkyl group or a phenyl group, and $R_3$ is a $C_{1-6}$ alkyl group or a $C_{3-8}$ cycloalkyl group. In another embodiment of the compound of Formula 1a or its pharmaceutically acceptable salt, $R_1$ is hydrogen; a $C_{1-6}$ alkyl group; a $C_{1-6}$ alkoxy group; an amino group; a $C_{1-6}$ alkylthio group; or a halogen group, $R_2$ is a $C_{3-8}$ cycloalkyl group or a phenyl group, and $R_3$ is a $C_{1-6}$ alkyl group or a $C_{3-8}$ cycloalkyl group. In still another embodiment of the compound of Formula 1a or its pharmaceutically acceptable salt, $R_1$ is hydrogen; a $C_{1-6}$ alkyl group; a $C_{1-6}$ alkoxy group; or an amino group, $R_2$ is a $C_{3-8}$ cycloalkyl group or a phenyl group, and $R_3$ is a $C_{1-6}$ alkyl group or a $C_{3-8}$ cycloalkyl group. In a preferable embodiment of the compound of Formula 1a or its pharmaceutically acceptable salt, $R_1$ is a $C_{1-6}$ alkoxy group or an amino group, $R_2$ is a phenyl group, and $R_3$ is a $C_{1-6}$ alkyl group or a $C_{3-8}$ cycloalkyl group.

In the compound of Formula 1a or its pharmaceutically acceptable salt, preferable compounds include a compound or its pharmaceutically acceptable salt selected from the group consisting of:

(S)-4-((1-(4-oxo-3-phenyl-5-(pyrimidin-5-yl)-3,4-dihydroquinazolin-2-yl)ethyl)amino)quinazoline-6-carbonitrile;
(S)-4-((1-(5-(2-aminopyrimidin-5-yl)-4-oxo-3-phenyl-3,4-dihydroquinazolin-2-yl)ethyl)amino)quinazoline-6-carbonitrile;
(S)-4-((1-(5-(2-methylpyrimidin-5-yl)-4-oxo-3-phenyl-3,4-dihydroquinazolin-2-yl)ethyl)amino)quinazoline-6-carbonitrile;
(S)-4-((1-(4-oxo-3-phenyl-5-(pyrimidin-5-yl)-3,4-dihydroquinazolin-2-yl)propyl)amino)quinazoline-6-carbonitrile;
(S)-4-((1-(5-(2-methoxypyrimidin-5-yl)-4-oxo-3-phenyl-3,4-dihydroquinazolin-2-yl)propyl)amino)quinazoline-6-carbonitrile;
(S)-4-((1-(5-(2-ethoxypyrimidin-5-yl)-4-oxo-3-phenyl-3,4-dihydroquinazolin-2-yl)propyl)amino)quinazoline-6-carbonitrile;
(S)-4-((1-(5-(2-(dimethylamino)pyrimidin-5-yl)-4-oxo-3-phenyl-3,4-dihydroquinazolin-2-yl)propyl)amino)quinazoline-6-carbonitrile;
(S)-4-((1-(5-(2-(methylsulfanyl)pyrimidin-5-yl)-4-oxo-3-phenyl-3,4-dihydroquinazolin-2-yl)propyl)amino)quinazoline-6-carbonitrile;
(S)-4-((1-(5-(2-methylpyrimidin-5-yl)-4-oxo-3-phenyl-3,4-dihydroquinazolin-2-yl)butyl)amino)quinazoline-6-carbonitrile;
(S)-4-((1-(5-(2-methoxypyrimidin-5-yl)-4-oxo-3-phenyl-3,4-dihydroquinazolin-2-yl)butyl)amino)quinazoline-6-carbonitrile;
(S)-4-((1-(5-(2-ethoxypyrimidin-5-yl)-4-oxo-3-phenyl-3,4-dihydroquinazolin-2-yl)butyl)amino)quinazoline-6-carbonitrile;
(S)-4-((1-(5-(2-aminopyrimidin-5-yl)-4-oxo-3-phenyl-3,4-dihydroquinazolin-2-yl)butyl)amino)quinazoline-6-carbonitrile;
(S)-4-((1-(5-(2-aminopyrimidin-5-yl)-4-oxo-3-phenyl-3,4-dihydroquinazolin-2-yl)-2-methylpropyl)amino)quinazoline-6-carbonitrile;
(S)-4-((cyclopropyl(4-oxo-3-phenyl-5-(pyrimidin-5-yl)-3,4-dihydroquinazolin-2-yl)methyl)amino)quinazoline-6-carbonitrile;
(S)-4-((cyclopropyl(5-(2-methoxypyrimidin-5-yl)-4-oxo-3-phenyl-3,4-dihydroquinazolin-2-yl)methyl)amino)quinazoline-6-carbonitrile;
(S)-4-((cyclopropyl(5-(2-ethoxypyrimidin-5-yl)-4-oxo-3-phenyl-3,4-dihydroquinazolin-2-yl)methyl)amino)quinazoline-6-carbonitrile;
(S)-4-((1-(3-cyclopropyl-4-oxo-5-(pyrimidin-5-yl)-3,4-dihydroquinazolin-2-yl)ethyl)amino)quinazoline-6-carbonitrile;
(S)-4-((1-(3-cyclopropyl-5-(2-methoxypyrimidin-5-yl)-4-oxo-3,4-dihydroquinazolin-2-yl)ethyl)amino)quinazoline-6-carbonitrile;
(S)-4-((1-(3-cyclopropyl-5-(2-ethoxypyrimidin-5-yl)-4-oxo-3,4-dihydroquinazolin-2-yl)ethyl)amino)quinazoline-6-carbonitrile;
(S)-4-((1-(3-cyclopropyl-4-oxo-5-(pyrimidin-5-yl)-3,4-dihydroquinazolin-2-yl)propyl)amino)quinazoline-6-carbonitrile;
(S)-4-((1-(5-(2-aminopyrimidin-5-yl)-3-cyclopropyl-4-oxo-3,4-dihydroquinazolin-2-yl)propyl)amino)quinazoline-6-carbonitrile;
(S)-2-(1-((5-fluoroquinazolin-4-yl)amino)ethyl)-3-phenyl-5-(pyrimidin-5-yl)quinazolin-4(3H)-one;
(S)-5-(2-aminopyrimidin-5-yl)-2-(1-((5-fluoroquinazolin-4-yl)amino)ethyl)-3-phenylquinazolin-4(3H)-one;
(S)-2-(1-((5-fluoroquinazolin-4-yl)amino)propyl)-3-phenyl-5-(pyrimidin-5-yl)quinazolin-4(3H)-one;
(S)-5-(2-aminopyrimidin-5-yl)-2-(1-((5-fluoroquinazolin-4-yl)amino)propyl)-3-phenylquinazolin-4(3H)-one;
(S)-5-(2-fluoropyrimidin-5-yl)-2-(1-((5-fluoroquinazolin-4-yl)amino)propyl)-3-phenylquinazolin-4(3H)-one;
(S)-2-(1-((5-fluoroquinazolin-4-yl)amino)propyl)-5-(2-methylpyrimidin-5-yl)-3-phenylquinazolin-4(3H)-one;
(S)-2-(1-((5-fluoroquinazolin-4-yl)amino)-2-methylpropyl)-3-phenyl-5-(pyrimidin-5-yl)quinazolin-4(3H)-one;

(S)-5-(2-aminopyrimidin-5-yl)-2-(1-((5-fluoroquinazolin-4-yl)amino)-2-methylpropyl)-3-phenylquinazolin-4(3H)-one;

(S)-2-(cyclopropyl((5-fluoroquinazolin-4-yl)amino)methyl)-3-phenyl-5-(pyrimidin-5-yl)quinazolin-4(3H)-one; and (S)-5-(2-aminopyrimidin-5-yl)-2-(cyclopropyl((5-fluoroquinazolin-4-yl)amino)meth yl)-3-phenylquinazolin-4(3H)-one.

In the compound of Formula 1a or its pharmaceutically acceptable salt, more preferable compounds include a compound or its pharmaceutically acceptable salt selected from the group consisting of:

(S)-4-((1-(4-oxo-3-phenyl-5-(pyrimidin-5-yl)-3,4-dihydroquinazolin-2-yl)ethyl)amino)quinazoline-6-carbonitrile;

(S)-4-((1-(5-(2-methylpyrimidin-5-yl)-4-oxo-3-phenyl-3,4-dihydroquinazolin-2-yl)ethyl)amino)quinazoline-6-carbonitrile;

(S)-4-((1-(4-oxo-3-phenyl-5-(pyrimidin-5-yl)-3,4-dihydroquinazolin-2-yl)propyl)amino)quinazoline-6-carbonitrile;

(S)-4-((1-(5-(2-methoxypyrimidin-5-yl)-4-oxo-3-phenyl-3,4-dihydroquinazolin-2-yl)propyl)amino)quinazoline-6-carbonitrile;

(S)-4-((1-(5-(2-ethoxypyrimidin-5-yl)-4-oxo-3-phenyl-3,4-dihydroquinazolin-2-yl)propyl)amino)quinazoline-6-carbonitrile;

(S)-4-((1-(5-(2-(methylsulfanyl)pyrimidin-5-yl)-4-oxo-3-phenyl-3,4-dihydroquinazolin-2-yl)propyl)amino)quinazoline-6-carbonitrile;

(S)-4-((1-(5-(2-methylpyrimidin-5-yl)-4-oxo-3-phenyl-3,4-dihydroquinazolin-2-yl)butyl)amino)quinazoline-6-carbonitrile;

(S)-4-((1-(5-(2-aminopyrimidin-5-yl)-4-oxo-3-phenyl-3,4-dihydroquinazolin-2-yl)-2-methylpropyl)amino)quinazoline-6-carbonitrile;

(S)-4-((cyclopropyl(4-oxo-3-phenyl-5-(pyrimidin-5-yl)-3,4-dihydroquinazolin-2-yl)methyl)amino)quinazoline-6-carbonitrile;

(S)-4-((cyclopropyl(5-(2-ethoxypyrimidin-5-yl)-4-oxo-3-phenyl-3,4-dihydroquinazolin-2-yl)methyl)amino)quinazoline-6-carbonitrile;

(S)-4-((1-(3-cyclopropyl-4-oxo-5-(pyrimidin-5-yl)-3,4-dihydroquinazolin-2-yl)ethyl)amino)quinazoline-6-carbonitrile;

(S)-4-((1-(3-cyclopropyl-5-(2-methoxypyrimidin-5-yl)-4-oxo-3,4-dihydroquinazolin-2-yl)ethyl)amino)quinazoline-6-carbonitrile;

(S)-4-((1-(3-cyclopropyl-5-(2-ethoxypyrimidin-5-yl)-4-oxo-3,4-dihydroquinazolin-2-yl)ethyl)amino)quinazoline-6-carbonitrile;

(S)-4-((1-(3-cyclopropyl-4-oxo-5-(pyrimidin-5-yl)-3,4-dihydroquinazolin-2-yl)propyl)amino)quinazoline-6-carbonitrile;

(S)-2-(1-((5-fluoroquinazolin-4-yl)amino)ethyl)-3-phenyl-5-(pyrimidin-5-yl)quinazolin-4(3H)-one;

(S)-5-(2-aminopyrimidin-5-yl)-2-(1-((5-fluoroquinazolin-4-yl)amino)ethyl)-3-phenylquinazolin-4(3H)-one;

(S)-2-(1-((5-fluoroquinazolin-4-yl)amino)propyl)-3-phenyl-5-(pyrimidin-5-yl)quinazolin-4(3H)-one;

(S)-5-(2-aminopyrimidin-5-yl)-2-(1-((5-fluoroquinazolin-4-yl)amino)propyl)-3-phenylquinazolin-4(3H)-one;

(S)-5-(2-fluoropyrimidin-5-yl)-2-(1-((5-fluoroquinazolin-4-yl)amino)propyl)-3-phenylquinazolin-4(3H)-one;

(S)-2-(1-((5-fluoroquinazolin-4-yl)amino)propyl)-5-(2-methylpyrimidin-5-yl)-3-phenylquinazolin-4(3H)-one;

(S)-2-(1-((5-fluoroquinazolin-4-yl)amino)-2-methylpropyl)-3-phenyl-5-(pyrimidin-5-yl)quinazolin-4(3H)-one;

(S)-5-(2-aminopyrimidin-5-yl)-2-(1-((5-fluoroquinazolin-4-yl)amino)-2-methylpropyl)-3-phenylquinazolin-4(3H)-one; and (S)-2-(cyclopropyl((5-fluoroquinazolin-4-yl)amino)methyl)-3-phenyl-5-(pyrimidin-5-yl)quinazolin-4(3H)-one.

In the compound of Formula 1a or its pharmaceutically acceptable salt, still more preferable compounds include a compound or its pharmaceutically acceptable salt selected from the group consisting of:

(S)-4-((1-(5-(2-methylpyrimidin-5-yl)-4-oxo-3-phenyl-3,4-dihydroquinazolin-2-yl)ethyl)amino)quinazoline-6-carbonitrile;

(S)-4-((1-(5-(2-ethoxypyrimidin-5-yl)-4-oxo-3-phenyl-3,4-dihydroquinazolin-2-yl)propyl)amino)quinazoline-6-carbonitrile;

(S)-4-((cyclopropyl(5-(2-ethoxypyrimidin-5-yl)-4-oxo-3-phenyl-3,4-dihydroquinazolin-2-yl)methyl)amino)quinazoline-6-carbonitrile;

(S)-4-((1-(3-cyclopropyl-4-oxo-5-(pyrimidin-5-yl)-3,4-dihydroquinazolin-2-yl)ethyl)amino)quinazoline-6-carbonitrile;

(S)-4-((1-(3-cyclopropyl-5-(2-methoxypyrimidin-5-yl)-4-oxo-3,4-dihydroquinazolin-2-yl)ethyl)amino)quinazoline-6-carbonitrile;

(S)-4-((1-(3-cyclopropyl-5-(2-ethoxypyrimidin-5-yl)-4-oxo-3,4-dihydroquinazolin-2-yl)ethyl)amino)quinazoline-6-carbonitrile;

(S)-2-(1-((5-fluoroquinazolin-4-yl)amino)ethyl)-3-phenyl-5-(pyrimidin-5-yl)quinazolin-4(3H)-one;

(S)-5-(2-aminopyrimidin-5-yl)-2-(1-((5-fluoroquinazolin-4-yl)amino)ethyl)-3-phenylquinazolin-4(3H)-one;

(S)-5-(2-aminopyrimidin-5-yl)-2-(1-((5-fluoroquinazolin-4-yl)amino)propyl)-3-phenylquinazolin-4(3H)-one;

(S)-2-(1-((5-fluoroquinazolin-4-yl)amino)propyl)-5-(2-methylpyrimidin-5-yl)-3-phenylquinazolin-4(3H)-one; and (S)-2-(1-((5-fluoroquinazolin-4-yl)amino)-2-methylpropyl)-3-phenyl-5-(pyrimidin-5-yl)quinazolin-4(3H)-one.

In the compound of Formula 1a or its pharmaceutically acceptable salt, particularly preferable compounds include a compound or its pharmaceutically acceptable salt selected from the group consisting of:

(S)-4-((1-(5-(2-ethoxypyrimidin-5-yl)-4-oxo-3-phenyl-3,4-dihydroquinazolin-2-yl)propyl)amino)quinazoline-6-carbonitrile;

(S)-4-((cyclopropyl(5-(2-ethoxypyrimidin-5-yl)-4-oxo-3-phenyl-3,4-dihydroquinazolin-2-yl)methyl)amino)quinazoline-6-carbonitrile;

(S)-5-(2-aminopyrimidin-5-yl)-2-(1-((5-fluoroquinazolin-4-yl)amino)ethyl)-3-phenylquinazolin-4(3H)-one; and (S)-5-(2-aminopyrimidin-5-yl)-2-(1-((5-fluoroquinazolin-4-yl)amino)propyl)-3-phenylquinazolin-4(3H)-one.

The compound of Formula 1a may be (S)-4-((1-(5-(2-ethoxypyrimidin-5-yl)-4-oxo-3-phenyl-3,4-dihydroquinazolin-2-yl)propyl)amino)quinazoline-6-carbonitrile or its pharmaceutically acceptable salt.

The compound of Formula 1a may be (S)-4-((cyclopropyl(5-(2-ethoxypyrimidin-5-yl)-4-oxo-3-phenyl-3,4-dihydroquinazolin-2-yl)methyl)amino)quinazoline-6-carbonitrile or its pharmaceutically acceptable salt.

The compound of Formula 1a may be (S)-5-(2-aminopyrimidin-5-yl)-2-(1-((5-fluoroquinazolin-4-yl)amino)ethyl)-3-phenylquinazolin-4(3H)-one or its pharmaceutically acceptable salt.

The compound of Formula 1a may be (S)-5-(2-aminopyrimidin-5-yl)-2-(1-((5-fluoroquinazolin-4-yl)amino)propyl)-3-phenylquinazolin-4(3H)-one or its pharmaceutically acceptable salt.

In another embodiment of the present invention, there is provided a compound of Formula 1b or its pharmaceutically acceptable salt wherein W is CH:

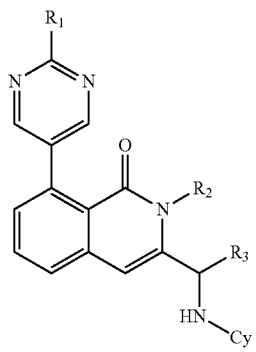

<Formula 1b> wherein, $R_1$, $R_2$, $R_3$ and Cy are the same as defined in the above.

In the compound of Formula 1b or its pharmaceutically acceptable salt, $R_1$ may be hydrogen; a $C_{1-6}$ alkyl group; a $C_{3-8}$ cycloalkyl group; a $C_{1-6}$ alkoxy group; an amino group; a $C_{1-6}$ alkylamino group; or a halogen group. Preferably, $R_1$ may be hydrogen; a $C_{1-6}$ alkyl group; a $C_{1-6}$ alkoxy group; an amino group; or a halogen group. More preferably, $R_1$ may be a $C_{1-6}$ alkyl group or a $C_{1-6}$ alkoxy group. In the compound of Formula 1b or its pharmaceutically acceptable salt, $R_2$ may be a phenyl group optionally substituted with halogen. Preferably, $R_2$ may be a phenyl group. In the compound of Formula 1b or its pharmaceutically acceptable salt, $R_3$ may be a $C_{1-6}$ alkyl group.

In an embodiment of the compound of Formula 1b or its pharmaceutically acceptable salt, $R_1$ is hydrogen; a $C_{1-6}$ alkyl group; a $C_{3-8}$ cycloalkyl group; a $C_{1-6}$ alkoxy group; an amino group; a $C_{1-6}$ alkylamino group; or a halogen group, $R_2$ is a phenyl group optionally substituted with halogen, and $R_3$ is a $C_{1-6}$ alkyl group. In another embodiment of the compound of Formula 1b or its pharmaceutically acceptable salt, $R_1$ is hydrogen; a $C_{1-6}$ alkyl group; a $C_{1-6}$ alkoxy group; an amino group; or a halogen group, $R_2$ is a phenyl group, and $R_3$ is a $C_{1-6}$ alkyl group. In a preferable embodiment of the compound of Formula 1b or its pharmaceutically acceptable salt, $R_1$ is a $C_{1-6}$ alkyl group or a $C_{1-6}$ alkoxy group, $R_2$ is a phenyl group, and $R_3$ is a $C_{1-6}$ alkyl group.

In the compound of Formula 1b or its pharmaceutically acceptable salt, preferable compounds include a compound or its pharmaceutically acceptable salt selected from the group consisting of:
(S)-4-((1-(1-oxo-2-phenyl-8-(pyrimidin-5-yl)-1,2-dihydroisoquinolin-3-yl)ethyl)amino)quinazoline-6-carbonitrile;
(S)-4-((1-(8-(2-methoxypyrimidin-5-yl)-1-oxo-2-phenyl-1,2-dihydroisoquinolin-3-yl)ethyl)amino)quinazoline-6-carbonitrile;
(S)-4-((1-(8-(2-ethoxypyrimidin-5-yl)-1-oxo-2-phenyl-1,2-dihydroisoquinolin-3-yl)ethyl)amino)quinazoline-6-carbonitrile;
(S)-4-((1-(8-(2-(dimethylamino)pyrimidin-5-yl)-1-oxo-2-phenyl-1,2-dihydroisoquinolin-3-yl)ethyl)amino)quinazoline-6-carbonitrile;
(S)-4-((1-(8-(2-methylpyrimidin-5-yl)-1-oxo-2-phenyl-1,2-dihydroisoquinolin-3-yl)ethyl)amino)quinazoline-6-carbonitrile;
(S)-4-((1-(8-(2-cyclopropylpyrimidin-5-yl)-1-oxo-2-phenyl-1,2-dihydroisoquinolin-3-yl)ethyl)amino)quinazoline-6-carbonitrile;
(S)-4-((1-(2-(4-fluorophenyl)-8-(2-methylpyrimidin-5-yl)-1-oxo-1,2-dihydroisoquinolin-3-yl)ethyl)amino)quinazoline-6-carbonitrile;
(S)-4-((1-(1-oxo-2-phenyl-8-(pyrimidin-5-yl)-1,2-dihydroisoquinolin-3-yl)propyl)amino)quinazoline-6-carbonitrile;
(S)-4-((1-(8-(2-methoxypyrimidin-5-yl)-1-oxo-2-phenyl-1,2-dihydroisoquinolin-3-yl)propyl)amino)quinazoline-6-carbonitrile;
(S)-4-((1-(8-(2-ethoxypyrimidin-5-yl)-1-oxo-2-phenyl-1,2-dihydroisoquinolin-3-yl)propyl)amino)quinazoline-6-carbonitrile;
(S)-4-((1-(8-(2-methylpyrimidin-5-yl)-1-oxo-2-phenyl-1,2-dihydroisoquinolin-3-yl)propyl)amino)quinazoline-6-carbonitrile;
(S)-8-(2-aminopyrimidin-5-yl)-3-(1-((5-fluoroquinazolin-4-yl)amino)ethyl)-2-phenylisoquinolin-1(2H)-one;
(S)-8-(2-fluoropyrimidin-5-yl)-3-(1-((5-fluoroquinazolin-4-yl)amino)ethyl)-2-phenylisoquinolin-1(2H)-one;
(S)-3-(1-((5-fluoroquinazolin-4-yl)amino)-2-methylpropyl)-2-phenyl-8-(pyrimidin-5-yl)isoquinolin-1(2H)-one;
(S)-8-(2-aminopyrimidin-5-yl)-3-(1-((5-fluoroquinazolin-4-yl)amino)-2-methylpropyl)-2-phenylisoquinolin-1(2H)-one; and
(S)-3-(1-((5-fluoroquinazolin-4-yl)amino)-2-methylpropyl)-8-(2-methylpyrimidin-5-yl)-2-phenylisoquinolin-1(2H)-one.

In the compound of Formula 1b or its pharmaceutically acceptable salt, more preferable compounds include a compound or its pharmaceutically acceptable salt selected from the group consisting of:
(S)-4-((1-(8-(2-ethoxypyrimidin-5-yl)-1-oxo-2-phenyl-1,2-dihydroisoquinolin-3-yl)ethyl)amino)quinazoline-6-carbonitrile;
(S)-4-((1-(8-(2-methylpyrimidin-5-yl)-1-oxo-2-phenyl-1,2-dihydroisoquinolin-3-yl)ethyl)amino)quinazoline-6-carbonitrile;
(S)-4-((1-(8-(2-ethoxypyrimidin-5-yl)-1-oxo-2-phenyl-1,2-dihydroisoquinolin-3-yl)propyl)amino)quinazoline-6-carbonitrile;
(S)-4-((1-(8-(2-methylpyrimidin-5-yl)-1-oxo-2-phenyl-1,2-dihydroisoquinolin-3-yl)propyl)amino)quinazoline-6-carbonitrile;
(S)-8-(2-fluoropyrimidin-5-yl)-3-(1-((5-fluoroquinazolin-4-yl)amino)ethyl)-2-phenylisoquinolin-1(2H)-one;
(S)-3-(1-((5-fluoroquinazolin-4-yl)amino)-2-methylpropyl)-2-phenyl-8-(pyrimidin-5-yl)isoquinolin-1(2H)-one;
(S)-8-(2-aminopyrimidin-5-yl)-3-(1-((5-fluoroquinazolin-4-yl)amino)-2-methylpropyl)-2-phenylisoquinolin-1(2H)-one; and
(S)-3-(1-((5-fluoroquinazolin-4-yl)amino)-2-methylpropyl)-8-(2-methylpyrimidin-5-yl)-2-phenylisoquinolin-1(2H)-one.

In the compound of Formula 1b or its pharmaceutically acceptable salt, particularly preferable compounds include a compound or its pharmaceutically acceptable salt selected from the group consisting of:
(S)-4-((1-(8-(2-ethoxypyrimidin-5-yl)-1-oxo-2-phenyl-1,2-dihydroisoquinolin-3-yl)ethyl)amino)quinazoline-6-carbonitrile;

(S)-4-((1-(8-(2-methylpyrimidin-5-yl)-1-oxo-2-phenyl-1,2-dihydroisoquinolin-3-yl)ethyl)amino)quinazoline-6-carbonitrile; and (S)-4-((1-(8-(2-methylpyrimidin-5-yl)-1-oxo-2-phenyl-1,2-dihydroisoquinolin-3-yl)propyl)amino)quinazoline-6-carbonitrile.

The compound of Formula 1b may be (S)-4-((1-(8-(2-ethoxypyrimidin-5-yl)-1-oxo-2-phenyl-1,2-dihydroisoquinolin-3-yl)ethyl)amino)quinazoline-6-carbonitrile or its pharmaceutically acceptable salt.

The compound of Formula 1b may be (S)-4-((1-(8-(2-methylpyrimidin-5-yl)-1-oxo-2-phenyl-1,2-dihydroisoquinolin-3-yl)ethyl)amino)quinazoline-6-carbonitrile or its pharmaceutically acceptable salt.

The compound of Formula 1b may be (S)-4-((1-(8-(2-methylpyrimidin-5-yl)-1-oxo-2-phenyl-1,2-dihydroisoquinolin-3-yl)propyl)amino)quinazoline-6-carbonitrile or its pharmaceutically acceptable salt.

The compound of Formula 1 or its pharmaceutically acceptable salt may have substituents containing asymmetric carbon (for example, the substituent $R_3$) and therefore be in the form of racemic mixture (RS) or in forms of optical isomers, such as (R) or (S) isomer. The compound of Formula 1 or its pharmaceutically acceptable salt comprises both racemic mixture (RS) and optical isomers such as (R) or (S) isomer.

The compound of Formula 1 of the present invention may be in a pharmaceutically acceptable salt form. The salt may be a conventional acid addition salt form, which includes, but not limited thereto, e.g., salts derived from an inorganic acid such as hydrochloric acid, hydrobromic acid, sulfuric acid, phosphoric acid, nitric acid or carbonic acid; and salts derived from an organic acid such as citric acid, acetic acid, lactic acid, tartaric acid, maleic acid, fumaric acid, lactobionic acid, salicylic acid, malonic acid, formic acid, propionic acid, oxalic acid, trifluoroacetic acid, benzoic acid, gluconic acid, methanesulfonic acid, glycolic acid, succinic acid, 4-toluenesulfonic acid, glutamic acid, or aspartic acid. And also, the salt includes a conventional metal salt form, e.g., salts derived from an alkali metal such as lithium, sodium, or potassium; salts derived from an alkaline earth metal such as calcium or magnesium; or a chromium salt.

The compound of Formula 1 or its pharmaceutically acceptable salt of the present invention may be prepared according to various methods. For example, the compound of Formula 1 or its pharmaceutically acceptable salt of the present invention may be prepared according to the following exemplary reaction schemes 1 to 3, but not limited thereto.

<Reaction Scheme 1>

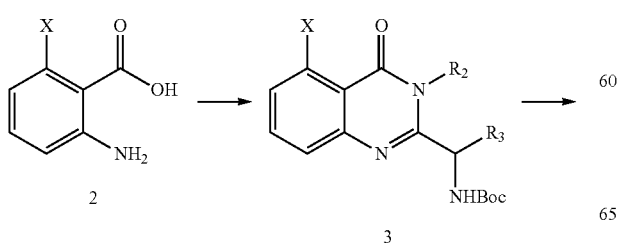

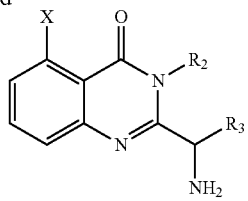

In the above Reaction Scheme 1, X is halogen, Boc is an amino-protecting group (for example, tert-butoxycarbonyl), and $R_2$ and $R_3$ are the same as defined in the above.

The compound of Formula 3 may be prepared by coupling the compound of Formula 2 with an amino acid (e.g., N-(tert-butoxycarbonyl)-L-alanine, etc.) in the presence of triphenyl phosphite and pyridine at about 70° C. and then dehydrogenating with an appropriate aniline derivative. The protecting group in the compound of Formula 3 may be removed through the reaction with an acid, such as hydrochloric acid or trifluoroacetic acid, to obtain the compound of Formula 4 in the form of an acid addition salt. The reactions of the Reaction Scheme 1 may be performed by reference to the methods disclosed in e.g., Bioorganic & medicinal Chemistry, Vol 16, Issue 5, 2008, 2570-2578.

<Reaction Scheme 2>

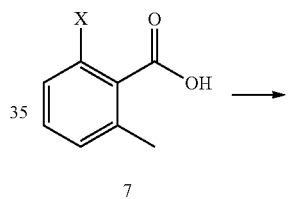

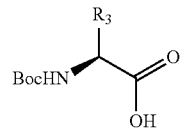

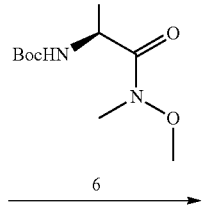

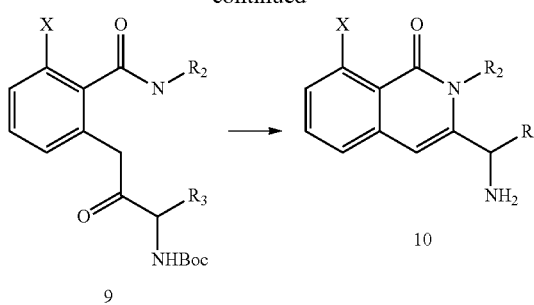
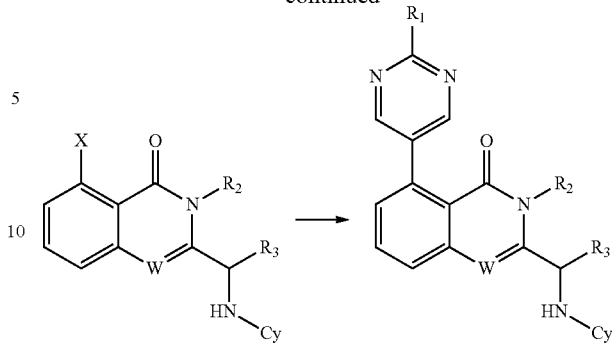

In the above Reaction Scheme 2, X is halogen, Boc is an amino-protecting group (for example, tert-butoxycarbonyl), and $R_2$ and $R_3$ are the same as defined in the above.

The compound of Formula 6 may be prepared by coupling the compound of Formula 5 (e.g., an S-isomer) with N,O-dimethylhydroxylamine in the presence of triethylamine, along with the use of hydroxybenzotriazole (HOBt) and 1-ethyl-3-(3'-dimethylaminopropyl)carbodiimide (EDC). The compound of Formula 8 may be prepared by reacting the compound of Formula 7 with a chlorinating agent in the presence of a base (e.g., triethylamine), followed by reacting with $R_2$—$NH_2$. The compound of Formula 8 may be dehydrogenated by using n-butyllithium dissolved in hexanes at −78° C. under argon atmosphere. After adding the compound of Formula 6 thereto, the temperature of the reaction mixture is controlled to −50° C. The reaction mixture is quenched with water to isolate the compound of Formula 9. In an embodiment, the magnesium anion of the compound of Formula 6 may be produced by using weakly nucleophilic organomagnesium species such as isopropylmagnesium chloride before the addition to the divalent anion. The compound of Formula 10 may be prepared by reacting the compound of Formula 9 with an acid (e.g., hydrochloric acid) in a solvent (e.g., methanol) and then basifying with a sodium carbonate or ammonium hydroxide solution.

<Reaction Scheme 3>

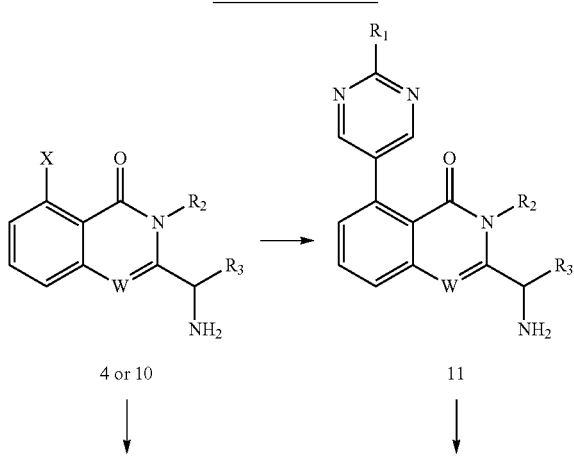

In the above Reaction Scheme 3, X is halogen, and $R_1$, $R_2$, $R_3$ and Cy are the same as defined in the above.

The compound of Formula 1 may be prepared by coupling the compound of Formula 4 or 10 with 4-chloroquinazoline-6-carbonitrile or 4-chloro-5-fluoroquinazoline in the presence of a base such as triethylamine, N,N-diisopropylethylamine, or ammonia to produce the compound of Formula 12 and then performing the Suzuki reaction with the use of $R_1$-pyrimidine-5-boronic acid.

And also, the compound of Formula 3 (i.e., the compound having an amino-protecting group) or the compound obtained by introducing an amino-protecting group to the compound of Formula 10 is subject to the Suzuki reaction, followed by removing the amino-protecting group to prepare the compound of Formula 11. And also, the compound of Formula 1 may be prepared by coupling the compound of Formula 11 with 4-chloroquinazoline-6-carbonitrile or 4-chloro-5-fluoroquinazoline in the presence of a base, according to the same methods as in the above. The introduction of an amino-protecting group to the compound of Formula 10 may be performed by using an amino-protecting group, such as di-tert-butyl dicarbonate, in the presence of a base such as triethylamine.

The Suzuki reaction may be carried out typically by using a palladium catalyst. The palladium catalyst includes tetrakis(triphenylphosphine)palladium(0), palladium(II) acetate, dichloro{1,1'-bis(diphenylphosphino)ferrocene}palladium (II), etc. The base includes an inorganic base such as cesium carbonate ($Cs_2CO_3$), sodium carbonate ($Na_2CO_3$), potassium carbonate ($K_2CO_3$), tripotassium phosphate ($K_3PO_4$). The reaction may be performed in a non-polar organic solvent such as toluene or in a polar organic solvent such as 1,4-dioxane, tetrahydrofuran, acetonitrile, 1,2-dimethoxyethane, or N,N-dimethylformamide, at 50° C. to 150° C., preferably at 80° C. to 110° C. Other reaction conditions, including the reaction time, may be in accordance with known methods regarding the Suzuki reaction.

The quinazoline derivative according to the present invention, i.e., the compound of Formula 1 or its pharmaceutically acceptable salt has a selective inhibitory activity against the PI3Kδ subunit, and therefore can be usefully applied for preventing or treating PI3Kδ subunit-mediated diseases, e.g., a respiratory disease, an inflammatory disease, or a proliferative disease, along with avoiding side effects such as lymphopenia-associated inflammatory responses.

Therefore, the present invention includes, within its scope, a pharmaceutical composition for selectively inhibiting phosphatidylinositol 3-kinase delta subunit, comprising a therapeutically effective amount of the compound of Formula 1 or its pharmaceutically acceptable salt as an active ingredient.

For example, the present invention includes, within its scope, a pharmaceutical composition for preventing or treating a respiratory disease, an inflammatory disease, or a proliferative disease. The respiratory disease and the inflammatory disease include e.g., asthma, chronic obstructive pulmonary disease (COPD), idiopathic pulmonary fibrosis, allergy (or anaphylaxis), psoriasis, rheumatoid arthritis, and autoimmune diseases. The proliferative disease include cancer such as breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, and lymphoma.

In an embodiment, the present invention provides a pharmaceutical composition for preventing or treating a proliferative disease. In another embodiment, the present invention provides a pharmaceutical composition for preventing or treating cancer, comprising a therapeutically effective amount of the compound of Formula 1 or its pharmaceutically acceptable salt as an active ingredient. The cancer includes breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, lymphoma, and so on.

And also, it has been found by the present invention that co-administration of the compound of Formula 1 or its pharmaceutically acceptable salt with an immune-checkpoint inhibitor, e.g., a negative regulating antibody of T-lymphocyte activation, exhibits synergistic anticancer activity. The immune-checkpoint inhibitor includes an anti-PDL1 antibody, an anti-PD1 antibody, an anti-CTLA4 antibody, and so on.

Therefore, in still another embodiment, the present invention provides a pharmaceutical composition for preventing or treating cancer, comprising a therapeutically effective amount of the compound of Formula 1 or its pharmaceutically acceptable salt in combination with a therapeutically effective amount of an immune-checkpoint inhibitor, wherein the combination exhibits synergistic anticancer activity. The cancer includes breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, lymphoma, and so on. In the pharmaceutical composition, the compound of Formula 1 or its pharmaceutically acceptable salt and the immune-checkpoint inhibitor may be formulated into a dosage form having a single compartment (i.e., into a same dosage form) or into a dosage form having two or more compartments (i.e., into same dosage forms or into different dosage forms). The two or more compartments may be the dosage forms administered through the same administration route or through the different administration route. For example, two or more compartments may be the dosage forms administered orally or parenterally, respectively.

The pharmaceutical composition of the present invention may comprise a pharmaceutically acceptable carrier, such as diluents, disintegrants, sweeteners, lubricants, or flavoring agents. The pharmaceutical composition may be formulated to an oral dosage form such as tablets, capsules, powders, granules, suspensions, emulsions, or syrups; or a parenteral dosage form such as solutions for external use, suspensions for external use, emulsions for external use, gels (e.g., ointment), inhalations, nebulizations, injections. The dosage form may be various forms, e.g., dosage forms for single administration or for multiple administrations.

The pharmaceutical composition of the present invention may comprise, for example, a diluent (e.g., lactose, corn starch, etc); a lubricant (e.g., magnesium stearate); an emulsifying agent; a suspending agent; a stabilizer; and/or an isotonic agent. If necessary, the composition further comprises sweeteners and/or flavoring agents.

The composition of the present invention may be administered orally or parenterally, including inhalant, intravenous, intraperitoneal, subcutaneous, rectal and topical routes of administration. Therefore, the composition of the present invention may be formulated into various forms such as tablets, capsules, aqueous solutions or suspensions. In the case of tablets for oral administration, carriers such as lactose, corn starch, and lubricating agents, e.g. magnesium stearate, are conventionally used. In the case of capsules for oral administration, lactose and/or dried corn starch can be used as a diluent. When an aqueous suspension is required for oral administration, the active ingredient may be combined with emulsifying and/or suspending agents. If desired, certain sweetening and/or flavoring agents may be used. For intramuscular, intraperitoneal, subcutaneous and intravenous administration, sterile solutions of the active ingredient are usually prepared, and the pH of the solutions should be suitably adjusted and buffered. For intravenous administration, the total concentration of solutes should be controlled in order to render the preparation isotonic. The composition of the present invention may be in the form of an aqueous solution containing pharmaceutically acceptable carriers, e.g., saline having a pH level of 7.4. The solutions may be introduced into a patient's intramuscular blood-stream by local bolus injection.

The quinazoline derivative, i.e., the compound of Formula 1 or its pharmaceutically acceptable salt may be administered in a therapeutically effective amount ranging from about 0.0001 mg/kg to about 100 mg/kg per day to a subject patient. Of course, the dosage may be changed according to the patient's age, weight, susceptibility, symptom, or activity of the compound. And also, the immune-checkpoint inhibitor may be administered in a known therapeutically effective amount of the respective antibody, which may be appropriately controlled by a person skilled in the art.

The present invention includes, within its scope, a method for selectively inhibiting phosphatidylinositol 3-kinase delta subunit in a mammal, comprising administering a therapeutically effective amount of the compound of Formula 1 or its pharmaceutically acceptable salt to the mammal in need thereof.

For example, the present invention includes, within its scope, a method for treating a respiratory disease, an inflammatory disease, or a proliferative disease. The respiratory disease and the inflammatory disease include e.g., asthma, chronic obstructive pulmonary disease (COPD), idiopathic pulmonary fibrosis, allergy (or anaphylaxis), psoriasis, rheumatoid arthritis, and autoimmune diseases. The proliferative disease include cancer such as breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, and lymphoma.

In an embodiment, the present invention provides a method for treating a proliferative disease, preferably cancer, in a mammal, comprising administering a therapeutically effective amount of the compound of Formula 1 or its pharmaceutically acceptable salt to the mammal in need thereof. The cancer includes breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, lymphoma, and so on.

And also, the present invention provides a method for treating cancer in a mammal, which comprises administering a therapeutically effective amount of the compound of Formula 1 or its pharmaceutically acceptable salt in combination with a therapeutically effective amount of an immune-checkpoint inhibitor to the mammal in need thereof, wherein the combination exhibits synergistic anticancer activity. In the combinatory administration, the respective active ingredients may be administered at the same time or separately; and through the same administration route or through the different administration routes. The cancer includes breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, lymphoma, and so on.

The present invention also provides a use of the compound of Formula 1 or its pharmaceutically acceptable salt for the manufacture of a medicament for selectively inhibiting phosphatidylinositol 3-kinase delta subunit in a mammal.

For example, the present invention includes, within its scope, a use of the compound of Formula 1 or its pharmaceutically acceptable salt for the manufacture of a medicament for preventing or treating a respiratory disease, an inflammatory disease, or a proliferative disease. The respiratory disease and the inflammatory disease include e.g., asthma, chronic obstructive pulmonary disease (COPD), idiopathic pulmonary fibrosis, allergy (or anaphylaxis), psoriasis, rheumatoid arthritis, and autoimmune diseases. The proliferative disease include cancer such as breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, and lymphoma.

In an embodiment, the present invention provides a use of the compound of Formula 1 or its pharmaceutically acceptable salt for the manufacture of a medicament for preventing or treating a proliferative disease, preferably cancer. The cancer includes breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, lymphoma, and so on.

And also, the present invention provides a use of the compound of Formula 1 or its pharmaceutically acceptable salt in combination with an immune-checkpoint inhibitor for the manufacture of a medicament for preventing or treating cancer. In the combination, the respective active ingredients may be administered at the same time or separately; and through the same administration route or through the different administration routes. The cancer includes breast cancer, bladder cancer, colorectal cancer, glioma, glioblastoma, lung cancer, hepatocellular carcinoma, stomach cancer, melanoma, thyroid cancer, endometrial cancer, kidney cancer, cervical cancer, pancreatic cancer, esophageal cancer, prostate cancer, brain cancer, cholangiocarcinoma, ovarian cancer, tuberous sclerosis, alveolar rhabdomyosarcoma, leukemia, lymphoma, and so on.

The following examples and experimental examples are provided for illustration purposes only, and are not intended to limit the scope of the invention.

The analyses of the compounds prepared in the following Preparations and Examples were carried out as follows: Nuclear magnetic resonance (NMR) spectrum analysis was carried out using Bruker 400 MHz spectrometer and chemical shifts thereof were analyzed in ppm. Column chromatography was carried out on silica gel (Merck, 70-230 mesh). Unless otherwise described, all starting materials were purchased commercially and used without further purification. All reactions and chromatographic fractions were analyzed by thin layer chromatography (TLC) on a 250 nm silica gel plate and visualized with ultraviolet or iodine ($I_2$) staining. The product and intermediates were purified by flash chromatography or reverse phase HPLC.

Preparation 1. (S)-2-(1-aminoethyl)-5-chloro-3-phenylquinazolin-4(3H)-one hydrochloride Step 1. tert-butyl (1-(5-chloro-4-oxo-3-phenyl-3,4-dihydroquinazolin-2-yl)ethyl)carbamate To a solution of 2-amino-6-chlorobenzoic acid (1.00 g, 7.29 mmol), N-(tert-butoxycarbonyl)-L-alanine (1.28 g, 7.29 mmol) in anhydrous pyridine (4 ml), was slowly added triphenyl phosphite (4.8 mL, 18.2 mmol). The reaction mixture was stirred at 70° C. for 2 hours and aniline (798 mL, 8.95 mmol) was added thereto. The reaction mixture was stirred at the same temperature for 4 hours and then concentrated under reduced pressure. The resulting residue was diluted with ethyl acetate, washed with a saturated sodium bicarbonate solution two times, dried over anhydrous magnesium sulfate, and then concentrated under reduced pressure. The resulting residue was purified by silica gel column chromatography (n-hexane/ethyl acetate=10/1, v/v) to give 450 mg of the titled compound as a white solid.

Step 2. (S)-2-(1-aminoethyl)-5-chloro-3-phenylquinazolin-4(3H)-one Hydrochloride To a solution of tert-butyl (1-(5-chloro-4-oxo-3-phenyl-3,4-dihydroquinazolin-2-yl)ethyl)carbamate (450 mg, 1.07 mmol) prepared in Step 1 in dichloromethane (5 ml), was slowly added a solution of hydrochloric acid in 1,4-dioxane (4 M, 2 ml). The reaction mixture was stirred at room temperature for 1 hour and then concentrated under reduced pressure. To the resulting residue, was added ethyl acetate. The mixture was stirred at room temperature for 1 hour and then filtered under reduced pressure. The resulting solid was dried to give 490 mg of the titled compound as a white solid. The product was used in the subsequent reaction without further purification.

Preparations 2 to 4

(S)-2-(1-aminopropyl)-5-chloro-3-phenylquinazolin-4 (3H)-one hydrochloride (Preparation 2), (S)-2-(1-aminobutyl)-5-chloro-3-phenylquinazolin-4(3H)-one hydrochloride (Preparation 3), and (S)-2-(amino(cyclopropyl) methyl)-5-chloro-3-phenylquinazolin-4(3H)-one hydrochloride (Preparation 4) were prepared in accordance with the same procedures as in Preparation 1, using (S)-2-(N-(tert-butoxycarbonyl)-amino)butyric acid, N-(tert-butoxycarbonyl)-L-norvaline, and (S)—N-Boc-cyclopropylglycine, instead of N-(tert-butoxycarbonyl)-L-alanine, respectively.

Preparation 5. (S)-2-(1-amino-2-methylpropyl)-5-bromo-3-phenylquinazolin-4(3H)-one Hydrochloride The titled compound was prepared in accordance with the same procedures as in Preparation 1, using 2-amino-6-bromobenzoic acid and N-(tert-butoxycarbonyl)-L-valine, instead of 2-amino-6-chlorobenzoic acid and N-(tert-butoxycarbonyl)-L-alanine.

Preparation 6. (S)-2-(1-aminoethyl)-5-chloro-3-cyclopropylquinazolin-4(3H)-one Hydrochloride The titled compound was prepared in accordance with the same procedures as in Preparation 1, using cyclopropylamine instead of aniline.

Preparation 7. (S)-2-(1-aminopropyl)-5-chloro-3-cyclopropylquinazolin-4(3H)-one Hydrochloride The titled compound was prepared in accordance with the same procedures as in Preparation 2, using cyclopropylamine instead of aniline.

Preparation 8. (S)-3-(1-aminoethyl)-8-chloro-2-phenylisoquinolin-1(2H)-one

Step 1. 2-chloro-6-methylbenzoyl Chloride

A solution of 2-chloro-6-methylbenzoic acid (171 mg, 1 mmol), oxalyl chloride (254 mg, 2 mmol), and N,N-dimethylformamide (5 uL) in dichloromethane (3 mL) was stirred at room temperature for 2 hours. The reaction mixture was concentrated under reduced pressure to give a residue as a yellow liquid. The residue was used in the subsequent reaction without further purification.

Step 2. 2-chloro-6-methyl-N-phenylbenzamide

A solution of aniline (93 mg, 1.1 mmol), triethylamine (202 mg, 2 mmol) in dichloromethane (3 mL) was stirred at room temperature for 10 minutes. 2-Chloro-6-methylbenzoyl chloride (202 mg, 2 mmol) prepared in Step 1 was slowly added to the solution, which was then stirred at room temperature for 1 hour. Water (3 mL) was added to the reaction mixture, which was then extracted with dichloromethane. The resulting extract was dried over anhydrous magnesium sulfate and then concentrated under reduced pressure. To the resulting residue, was added n-heptane. The mixture was stirred at room temperature for 30 minutes and then filtered under reduced pressure. The resulting solid was dried to give 214 mg of the titled compound as a white solid. (Yield: 87%)

Step 3. tert-butyl (S)-(1-(methoxy(methyl)amino)-1-oxopropan-2-yl)carbamate

While a mixture of N-(tert-butoxycarbonyl)-L-alanine (1 g, 5.3 mmol), triethylamine (2.9 mL, 21.1 mmol) and hydroxybenzotriazole (135 mg, 5.3 mmol) in anhydrous dichloromethane (20 mL) was stirred at 0° C., 1-ethyl-3-(3'-dimethylaminopropyl)carbodiimide (384.3 mg, 10.9 mmol) was slowly added thereto over 30 minutes. The reaction mixture was stirred at room temperature for 30 minutes and then N,O-dimethylhydroxylamine hydrochloride (568.7 mg, 5.8 mmol) was added thereto. The reaction mixture was stirred at room temperature for 20 hours and then quenched by water (100 mL). The organic layer was washed with water (2×1 L) and brine (500 mL), dried over anhydrous magnesium sulfate, filtered, and then concentrated under reduced pressure. The resulting residue was slurried in petroleum ether (200 mL), stirred at room temperature for 10 minutes, and then filtered. The resulting solid was dried in vacuo to give 1.1 g of the titled compound as a white solid.

Step 4. tert-butyl (S)-(4-(3-chloro-2-(phenylcarbamoyl)phenyl)-3-oxobutan-2-yl)carbamate A solution of 2-chloro-6-methyl-N-phenylbenzamide (246 mg, 1 mmol) prepared in Step 2 in anhydrous tetrahydrofuran (3 mL) was cooled to −78° C. and then a solution of n-butyllithium in hexane (2.5 M, 1 mL) was slowly added thereto over 20 minutes. The reaction mixture was stirred at the same temperature for 2 hours. A solution of tert-butyl (S)-(1-(methoxy(methyl)amino)-1-oxopropan-2-yl)carbamate (370 mg, 1.5 mmol) prepared in Step 3 in anhydrous tetrahydrofuran (5 mL) was added at −78° C. to the reaction mixture. Then, a solution of isopropylmagnesium chloride in tetrahydrofuran (0.9 mL) was slowly added to the reaction mixture for 20 minutes. The reaction mixture was stirred at the same temperature for 2 hours and then the reaction temperature thereof was increased to −50° C. The reaction mixture was quenched by water (3 mL) and then extracted with ethyl acetate. The extract was dried over anhydrous magnesium sulfate and then concentrated under reduced pressure. The resulting residue was purified by silica gel column chromatography (n-hexane/ethyl acetate=2/1, v/v) to give 185 mg of the titled compound as a colorless liquid. The product was used in the subsequent reaction without further purification.

Step 5. (S)-3-(1-aminoethyl)-8-chloro-2-phenylisoquinolin-1(2H)-one

To a solution of tert-butyl (S)-(4-(3-chloro-2-(phenylcarbamoyl)phenyl)-3-oxobutan-2-yl)carbamate (390 mg, 0.9 mmol) prepared in Step 4 in methanol (3 mL), was slowly added hydrochloric acid (1 mL) at room temperature. The reaction mixture was stirred at 60° C. for 3 hours, controlled to pH 9-10 with a saturated ammonium hydroxide solution, and then extracted with dichloromethane. The extract was dried over anhydrous magnesium sulfate and then concentrated under reduced pressure. The resulting residue was purified by silica gel column chromatography (dichloromethane/methanol=20/1, v/v) to give 189 mg of the titled compound as a white solid. (Yield: 67%)

Preparation 9. (S)-3-(1-aminoethyl)-8-chloro-2-(4-fluorophenyl)isoquinolin-1(2H)-one The titled compound was prepared in accordance with the same procedures as in Preparation 8, using 4-fluoroaniline instead of aniline.

Preparations 10 and 11

(S)-3-(1-aminopropyl)-8-chloro-2-phenylisoquinolin-1 (2H)-one (Preparation 10) and (S)-3-(1-amino-2-methylpropyl)-8-chloro-2-phenylisoquinolin-1(2H)-one (Preparation 11) were prepared in accordance with the same procedures as in Preparation 8, using (S)-2-(N-(tert-butoxycarbonyl)-amino)butyric acid and N-(tert-butoxycarbonyl)-L-valine, instead of N-(tert-butoxycarbonyl)-L-alanine, respectively.

Preparation 12. (S)-4-((1-(5-chloro-4-oxo-3-phenyl-3,4-dihydroquinazolin-2-yl)ethyl)amino)quinazoline-6-carbonitrile To a solution of (S)-2-(1-aminoethyl)-5-chloro-3-phenylquinazolin-4(3H)-one hydrochloride (16.9 mg, 0.052 mmol) prepared in Preparation 1 and 4-chloroquinazoline-6-carbonitrile (10 mg, 0.052 mmol) in isopropyl alcohol (1 mL), was slowly added N,N-diisopropylethylamine (28 uL, 0.16 mmol). The reaction mixture was stirred at 80° C. for 2 hours, cooled to room temperature, and then concentrated under reduced pressure. The residue in a yellow liquid was purified by silica gel column chromatography (n-hexane/ethyl acetate=1/1, v/v) to give 14 mg of the titled compound as a white solid.
$^1$H-NMR (400 MHz, CDCl3) δ 8.63 (s, 1H), 8.27 (s, 1H), 7.88 (s, 2H), 7.64~7.57 (m, 5H), 7.50 (m, 2H), 7.40 (m, 1H), 7.29 (m, 1H), 5.24 (m, 1H), 1.52 (d, 3H)

Preparations 13 to 18

The titled compounds of Preparations 13 to 18 were prepared in accordance with the same procedures as in Preparation 12, using the compounds prepared in Preparations 2 to 7, instead of (S)-2-(1-aminoethyl)-5-chloro-3-phenylquinazolin-4(3H)-one hydrochloride, respectively.

Preparation 13. (S)-4-((1-(5-chloro-4-oxo-3-phenyl-3,4-dihydroquinazolin-2-yl)propyl)amino)quinazoline-6-carbonitrile $^1$H-NMR (400 MHz, CDCl$_3$) δ 8.61 (s, 1H), 8.30 (s, 1H), 7.90 (s, 2H), 7.63 (m, 5H), 7.55 (m, 1H), 7.48 (m, 2H), 7.04 (d, 1H), 5.27 (m, 1H), 2.03 (m, 1H), 1.85 (m, 1H), 0.86 (t, 3H)

Preparation 14. (S)-4-((1-(5-chloro-4-oxo-3-phenyl-3,4-dihydroquinazolin-2-yl)butyl)amino)quinazoline-6-carbonitrile $^1$H-NMR (400 MHz, CDCl$_3$) δ 8.63 (s, 1H), 8.32 (s, 1H), 7.90 (s, 2H), 7.64-7.57 (m, 5H), 7.50 (m, 2H), 7.39 (d, 1H), 6.97 (d, 1H), 5.35 (m, 1H), 1.86 (m, 2H), 1.36 (m, 1H), 1.24 (m, 1H), 0.68 (t, 3H)

Preparation 15. (S)-4-(((5-chloro-4-oxo-3-phenyl-3,4-dihydroquinazolin-2-yl)(cyclopropyl)methyl)amino)quinazoline-6-carbonitrile $^1$H-NMR (400 MHz, CDCl$_3$) δ 8.60 (s, 1H), 8.27 (s, 1H), 7.90 (s, 2H), 7.63 (d, 2H), 7.58 (m, 3H), 7.50 (m, 2H), 7.46 (m, 1H), 6.97 (d, 1H), 4.98 (m, 1H), 1.36 (m, 1H), 0.58 (m, 2H), 0.35 (m, 1H), 0.12 (m, 1H)

Preparation 16. (S)-4-((1-(5-bromo-4-oxo-3-phenyl-3,4-dihydroquinazolin-2-yl)-2-methylpropyl)amino)quinazoline-6-carbonitrile $^1$H-NMR (400 MHz, CDCl$_3$) δ 8.59 (s, 1H), 8.26 (s, 1H), 7.91 (s, 2H), 7.74 (m, 2H), 7.61 (m, 4H), 7.39 (m, 1H), 7.30 (m, 1H), 6.77 (d, 1H), 5.44 (m, 1H), 2.26 (m, 1H), 0.99 (d, 3H), 0.83 (d, 3H)

Preparation 17. (S)-4-((1-(5-chloro-3-cyclopropyl-4-oxo-3,4-dihydroquinazolin-2-yl)ethyl)amino)quinazoline-6-carbonitrile $^1$H-NMR (400 MHz, CDCl$_3$) δ 8.74 (s, 1H), 8.28 (s, 1H), 7.93 (s, 2H), 7.62 (d, 2H), 7.47 (m, 1H), 7.42 (m, 1H), 6.33 (m, 1H), 3.09 (m, 1H), 1.71 (d, 3H), 1.48 (m, 2H), 1.12 (m, 1H), 1.01 (m, 1H)

Preparation 18. (S)-4-((1-(5-chloro-3-cyclopropyl-4-oxo-3,4-dihydroquinazolin-2-yl)propyl)amino)quinazoline-6-carbonitrile $^1$H-NMR (400 MHz, CDCl$_3$) δ 8.73 (s, 1H), 8.36 (s, 1H), 7.92 (s, 2H), 7.57 (m, 2H), 7.46 (m, 1H), 7.26 (m, 1H), 6.39 (m, 1H), 3.10 (m, 1H), 2.19 (m, 1H), 2.00 (m, 1H), 1.49 (m, 2H), 1.06 (t, 3H), 0.88 (m, 2H)

Preparations 19 to 22

The titled compounds of Preparations 19 to 22 were prepared in accordance with the same procedures as in Preparation 12, using 4-chloro-5-fluoroquinazoline instead of 4-chloroquinazoline-6-carbonitrile; and the compounds prepared in Preparations 1, 2, 4, and 5, instead of (S)-2-(1-aminoethyl)-5-chloro-3-phenylquinazolin-4(3H)-one hydrochloride, respectively.

Preparation 19. (S)-5-chloro-2-(1-((5-fluoroquinazolin-4-yl)amino)ethyl)-3-phenylquinazolin-4(3H)-one $^1$H-NMR (400 MHz, CDCl$_3$) δ 8.49 (s, 1H), 7.83 (m, 1H), 7.61 (m, 7H), 7.49 (m, 2H), 7.38 (m, 1H), 7.13 (m, 1H), 5.21 (m, 1H), 1.48 (d, 3H)

Preparation 20. (S)-5-chloro-2-(1-((5-fluoroquinazolin-4-yl)amino)propyl)-3-phenylquinazolin-4(3H)-one $^1$H-NMR (400 MHz, CDCl$_3$) δ 8.47 (s, 1H), 7.66~7.57 (m, 7H), 7.48 (m, 2H), 7.37 (m, 1H), 7.14 (m, 1H), 5.22 (m, 1H), 1.97 (m, 1H), 1.77 (m, 1H), 0.87 (t, 3H)

Preparation 21. (S)-5-chloro-2-(cyclopropyl((5-fluoroquinazolin-4-yl)amino)methyl)-3-phenylquinazolin-4(3H)-one $^1$H-NMR (400 MHz, CDCl$_3$) δ 8.46 (s, 1H), 7.68~7.51 (m, 9H), 7.48 (m, 1H), 7.43 (m, 1H), 7.20 (m, 1H), 4.97 (m, 1H), 1.32 (m, 1H), 0.53 (m, 2H), 0.37 (m, 1H), 0.21 (m, 1H)

Preparation 22. (S)-5-bromo-2-(1-((5-fluoroquinazolin-4-yl)amino)-2-methylpropyl)-3-phenylquinazolin-4(3H)-one $^1$H-NMR (400 MHz, CDCl$_3$) δ 8.58 (s, 1H), 7.72 (m, 1H), 7.71~7.45 (m, 6H), 7.36 (m, 2H), 7.15 (m, 2H), 7.14 (m, 1H), 5.39 (m, 1H), 2.21 (m, 1H), 0.99 (d, 3H), 0.82 (d, 3H)

Preparations 23 to 25

The titled compounds of Preparations 23 to 25 were prepared in accordance with the same procedures as in Preparation 12, using the compounds prepared in Preparations 8 to 10, instead of (S)-2-(1-aminoethyl)-5-chloro-3-phenylquinazolin-4(3H)-one hydrochloride, respectively.

Preparation 23. (S)-4-((1-(8-chloro-1-oxo-2-phenyl-1,2-dihydroisoquinolin-3-yl)ethyl)amino)quinazoline-6-carbonitrile $^1$H-NMR (400 MHz, CDCl$_3$) δ 8.55 (s, 1H), 8.35 (s, 1H), 7.85 (m, 2H), 7.31 (m, 3H), 7.10 (m, 1H), 7.05 (m, 4H), 6.78 (br, 1H), 6.62 (s, 1H), 5.06 (m, 1H), 1.50 (d, 3H)

Preparation 24. (S)-4-((1-(8-chloro-2-(4-fluorophenyl)-1-oxo-1,2-dihydroisoquinolin-3-yl)ethyl)amino)quinazoline-6-carbonitrile $^1$H-NMR (400 MHz, CDCl$_3$) δ 8.57 (s, 1H), 8.44 (s, 1H), 7.95~7.80 (m, 2H), 7.48~7.39 (m, 3H), 7.33~7.29 (m, 2H), 7.20 (m, 1H), 6.91 (m, 1H), 6.73 (d, 1H), 6.62 (s, 1H), 5.06~5.01 (m, 1H), 1.52 (d, 3H)

Preparation 25. (S)-4-((1-(8-chloro-1-oxo-2-phenyl-1,2-dihydroisoquinolin-3-yl)propyl)amino)quinazoline-6-carbonitrile $^1$H-NMR (400 MHz, MeOD) δ 8.85 (s, 1H), 8.47 (s, 1H), 8.02 (d, 1H), 7.81 (d, 1H), 7.62~7.43 (m, 9H), 6.83 (s, 1H), 4.94 (m, 1H), 2.18 (m, 1H), 1.94 (m, 1H), 0.90 (t, 3H)

Preparations 26 and 27

The titled compounds of Preparations 26 and 27 were prepared in accordance with the same procedures as in Preparation 12, using 4-chloro-5-fluoroquinazoline instead of 4-chloroquinazoline-6-carbonitrile; and the compounds prepared in Preparations 8 and 11, instead of (S)-2-(1-aminoethyl)-5-chloro-3-phenylquinazolin-4(3H)-one hydrochloride, respectively.

Preparation 26. (S)-8-chloro-3-(1-((5-fluoroquinazolin-4-yl)amino)ethyl)-2-phenylisoquinolin-1(2H)-one $^1$H-NMR (400 MHz, CDCl$_3$) δ 8.50 (s, 1H), 7.64 (m, 2H), 7.50 (m, 2H), 7.44 (m, 2H), 7.37~7.30 (m, 4H), 7.17~7.12 (m, 1H), 6.67 (m, 1H), 6.60 (s, 1H), 5.06 (m, 1H), 1.50 (d, 3H)

Preparation 27. (S)-8-chloro-3-(1-((5-fluoroquinazolin-4-yl)amino)-2-methylpropyl)-2-phenylisoquinolin-1(2H)-one $^1$H-NMR (400 MHz, CDCl$_3$) δ 8.55 (s, 1H), 7.66 (m, 3H), 7.57 (m, 2H), 7.48 (m, 1H), 7.35 (m, 2H), 7.20 (m, 2H), 7.15 (m, 1H), 6.88 (m, 1H), 6.45 (m, 1H), 4.97 (m, 1H), 1.00 (d, 3H), 0.88 (d, 3H)

Example 1. (S)-4-((1-(4-oxo-3-phenyl-5-(pyrimidin-5-yl)-3,4-dihydroquinazolin-2-yl)ethyl)amino)quinazoline-6-carbonitrile To a mixture of (S)-4-((1-(5-chloro-4-oxo-3-phenyl-3,4-dihydroquinazolin-2-yl)ethyl)amino)quinazoline-6-carbonitrile (15 mg, 0.03 mmol) prepared in Preparation 12, pyrimidine-5-boronic acid (5.6 mg, 0.045 mmol), a 2N sodium carbonate solution (400 uL), and tetrakis(triphenylphosphine)palladium(0) (1.9 mg, 5 mol %), was slowly added 1,4-dioxane (1 mL). The reaction mixture was refluxed under stirring at 96° C. overnight and then cooled to room temperature. Distilled water was added to the reaction mixture, which was then extracted with dichloromethane. The extract was dried over anhydrous magnesium sulfate and then concentrated under reduced pressure to give a residue as a yellow liquid. The residue was purified by silica gel column chromatography (dichloromethane/methanol=9/1, v/v) to give 8.9 mg of the titled compound as a pale yellow solid.

$^1$H-NMR (400 MHz, CDCl$_3$) δ 9.14 (s, 1H), 8.71 (s, 2H), 8.64 (s, 1H), 8.29 (s, 1H), 7.88 (m, 3H), 7.85 (s, 1H), 7.57 (m, 2H), 7.50 (m, 2H), 7.33 (m, 3H), 5.26 (m, 1H), 1.58 (d, 3H)

Examples 2 to 47

The titled compounds of Examples 2 to 47 were prepared in accordance with the same procedures as in Example 1, using the compounds prepared in Preparation 12 to 27; and the corresponding substituted or unsubstituted pyrimidine-5-boronic acid.

Example 2. (S)-4-((1-(5-(2-aminopyrimidin-5-yl)-4-oxo-3-phenyl-3,4-dihydroquinazolin-2-yl)ethyl)amino)quinazoline-6-carbonitrile $^1$H-NMR (400 MHz, CDCl$_3$) δ 8.64 (s, 1H), 8.29 (s, 3H), 7.86 (s, 2H), 7.80 (m, 2H), 7.60~7.52 (m, 4H), 7.47 (m, 2H), 7.29 (m, 1H), 5.24 (m, 1H), 5.07 (s, 2H), 1.55 (d, 3H); (Yield: 54%)

Example 3. (S)-4-((1-(5-(2-methylpyrimidin-5-yl)-4-oxo-3-phenyl-3,4-dihydroquinazolin-2-yl)ethyl)amino)quinazoline-6-carbonitrile $^1$H-NMR (400 MHz, CDCl$_3$) δ 8.64 (s, 1H), 8.60 (s, 2H), 8.29 (s, 1H), 7.87 (m, 4H), 7.59 (m, 3H), 7.45 (m, 1H), 7.30 (m, 3H), 5.26 (m, 1H), 2.73 (s, 3H), 1.53 (d, 3H); (Yield: 52%)

Example 4. (S)-4-((1-(4-oxo-3-phenyl-5-(pyrimidin-5-yl)-3,4-dihydroquinazolin-2-yl)propyl)amino)quinazoline-6-carbonitrile $^1$H-NMR (400 MHz, CDCl$_3$) δ 9.13 (s, 1H), 8.69 (s, 2H), 8.63 (s, 1H), 8.30 (s, 1H), 7.92 (s, 2H), 7.90~7.82 (m, 2H), 7.62~7.53 (m, 3H), 7.43~7.35 (m, 1H), 7.34~7.28 (m, 2H), 6.99 (d, 1H), 5.32~5.24 (m, 1H), 2.04~1.98 (m, 1H), 1.89~1.75 (m, 1H), 0.88 (t, 3H); (Yield: 65%)

Example 5. (S)-4-((1-(5-(2-methoxypyrimidin-5-yl)-4-oxo-3-phenyl-3,4-dihydroquinazolin-2-yl)propyl)amino)quinazoline-6-carbonitrile $^1$H-NMR (400 MHz, CDCl$_3$) δ 8.62 (s, 1H), 8.46 (s, 2H), 8.34 (s, 1H), 7.91 (s, 2H), 7.84~7.81 (m, 2H), 7.62~7.53 (m, 3H), 7.43~7.37 (m, 1H), 7.32~7.27 (m, 2H), 7.12 (d, 1H), 5.29~5.24 (m, 1H), 4.00 (s, 3H), 2.05~1.96 (m, 1H), 1.89~1.76 (m, 1H), 0.88 (t, 3H); (Yield: 51%)

Example 6. (S)-4-((1-(5-(2-ethoxypyrimidin-5-yl)-4-oxo-3-phenyl-3,4-dihydroquinazolin-2-yl)propyl)amino)quinazoline-6-carbonitrile $^1$H-NMR (400 MHz, CDCl$_3$) δ 8.62 (s, 1H), 8.45 (s, 2H), 8.32 (s, 1H), 7.91 (s, 2H), 7.85~7.80 (m, 2H), 7.61~7.52 (m, 3H), 7.40 (d, 1H), 7.34~7.27 (m, 2H), 7.06 (d, 1H), 5.31~5.25 (m, 1H), 4.41 (q, 2H), 2.05~1.98 (m, 1H), 1.85~1.78 (m, 1H), 1.42 (t, 3H), 0.88 (t, 3H); (Yield: 67%)

Example 7. (S)-4-((1-(5-(2-(dimethylamino)pyrimidin-5-yl)-4-oxo-3-phenyl-3,4-dihydroquinazolin-2-yl)propyl)amino)quinazoline-6-carbonitrile $^1$H-NMR (400 MHz, CDCl$_3$) δ 8.61 (s, 1H), 8.31 (s, 1H), 8.29 (s, 2H), 7.91 (s, 2H), 7.83~7.74 (m, 2H), 7.60~7.51 (m, 3H), 7.38~7.34 (m, 1H), 733~7.27 (m, 2H), 7.13 (d, 1H), 5.30~5.26 (m, 1H), 3.17 (s, 6H), 2.05~1.96 (m, 1H), 1.83~1.76 (m, 1H), 0.88 (t, 3H); (Yield: 60%)

Example 8. (S)-4-((1-(5-(2-(methylsulfanyl)pyrimidin-5-yl)-4-oxo-3-phenyl-3,4-dihydroquinazolin-2-yl)propyl)amino)quinazoline-6-carbonitrile $^1$H-NMR (400 MHz, CDCl$_3$) δ 8.62 (s, 1H), 8.48 (s, 2H), 8.35 (s, 1H), 7.91 (s, 2H), 7.83 (d, 2H), 7.60~7.52 (m, 3H), 7.43~7.39 (m, 1H), 7.31~7.26 (m, 2H), 7.14 (d, 1H), 5.28~5.24 (m, 1H), 2.55 (s, 3H), 2.04~1.95 (m, 1H), 1.88~1.77 (m, 1H), 0.88 (t, 3H); (Yield: 44%)

Example 9. (S)-4-((1-(5-(2-methylpyrimidin-5-yl)-4-oxo-3-phenyl-3,4-dihydroquinazolin-2-yl)butyl)amino)quinazoline-6-carbonitrile $^1$H-NMR (400 MHz, CDCl$_3$) δ 8.64 (s, 1H), 8.59 (s, 2H), 8.33 (s, 1H), 7.91 (s, 2H), 7.82 (m, 2H), 7.61 (m, 3H), 7.56 (m, 1H), 7.30 (m, 2H), 6.98 (d, 1H), 5.38 (m, 1H), 2.73 (s, 3H), 1.84 (m, 2H), 1.34 (m, 1H), 1.13 (m, 1H), 0.69 (t, 3H); (Yield: 51%)

Example 10. (S)-4-((1-(5-(2-methoxypyrimidin-5-yl)-4-oxo-3-phenyl-3,4-dihydroquinazolin-2-yl)butyl)amino)quinazoline-6-carbonitrile $^1$H-NMR (400 MHz, CDCl$_3$) δ 8.64 (s, 1H), 8.46 (s, 2H), 8.30 (s, 1H), 7.91 (s, 2H), 7.80 (m, 2H), 7.59 (m, 3H), 7.46 (m, 1H), 7.30 (m, 2H), 6.94 (d, 1H), 5.37 (m, 1H), 4.00 (s, 3H), 1.84 (m, 2H), 1.36 (m, 1H), 1.24 (m, 1H), 0.69 (t, 3H); (Yield: 74%)

Example 11. (S)-4-((1-(5-(2-ethoxypyrimidin-5-yl)-4-oxo-3-phenyl-3,4-dihydroquinazolin-2-yl)butyl)amino)quinazoline-6-carbonitrile $^1$H-NMR (400 MHz, CDCl$_3$) δ 8.64 (s, 1H), 8.44 (s, 2H), 8.31 (s, 1H), 7.91 (s, 2H), 7.80 (m, 2H), 7.62~7.55 (m, 3H), 7.45 (d, 1H), 7.30 (m, 2H), 6.93 (d, 1H), 5.38 (m, 1H), 4.42 (q, 2H), 1.84 (m, 2H), 1.42 (t, 3H), 1.36 (m, 1H), 1.26 (m, 1H), 0.69 (t, 3H); (Yield: 51%)

Example 12. (S)-4-((1-(5-(2-aminopyrimidin-5-yl)-4-oxo-3-phenyl-3,4-dihydroquinazolin-2-yl)butyl)amino)quinazoline-6-carbonitrile $^1$H-NMR (400 MHz, CDCl$_3$) δ 8.65 (s, 1H), 8.35 (s, 1H), 8.28 (s, 2H), 7.91 (s, 2H), 7.78 (m, 2H), 7.63~7.55 (m, 3H), 7.45 (d, 1H), 7.33 (m, 2H), 7.00 (d, 1H), 5.38 (m, 1H), 5.04 (s, 2H), 1.85 (m, 2H), 1.36 (m, 1H), 1.24 (m, 1H), 0.68 (t, 3H); (Yield: 54%)

Example 13. (S)-4-((1-(5-(2-aminopyrimidin-5-yl)-4-oxo-3-phenyl-3,4-dihydroquinazolin-2-yl)-2-methylpropyl)amino)quinazoline-6-carbonitrile $^1$H-NMR (400 MHz, CDCl$_3$) δ 8.59 (s, 1H), 8.29 (s, 1H), 8.26 (s, 2H), 7.91 (s, 2H), 7.83~7.80 (m, 2H), 7.59~7.51 (m, 3H), 7.35~7.26 (m, 3H), 6.88 (d, 1H), 5.47~5.43 (m, 1H), 5.14 (brs, 2H), 2.34~2.23 (m, 1H), 1.01 (d, 3H), 0.84 (d, 3H); (Yield: 53%)

Example 14. (S)-4-((cyclopropyl(4-oxo-3-phenyl-5-(pyrimidin-5-yl)-3,4-dihydroquinazolin-2-yl)methyl)amino)quinazoline-6-carbonitrile $^1$H-NMR (400 MHz, CDCl$_3$) δ 9.13 (s, 1H), 8.70 (s, 2H), 8.60 (s, 1H), 8.32 (s, 1H), 7.89 (s, 2H), 7.86 (m, 2H), 7.57 (m, 2H), 7.49 (m, 2H), 7.30 (m, 1H), 7.13 (d, 1H), 4.95 (m, 1H), 1.39 (m, 1H), 0.60 (m, 2H), 0.40 (m, 1H), 0.18 (m, 1H); (Yield: 51%)

Example 15. (S)-4-((cyclopropyl(5-(2-methoxypyrimidin-5-yl)-4-oxo-3-phenyl-3,4-dihydroquinazolin-2-yl)methyl)amino)quinazoline-6-carbonitrile $^1$H-NMR (400 MHz, CDCl$_3$) δ 8.59 (s, 1H), 8.47 (s, 2H), 8.39 (s, 1H), 7.86 (m, 2H), 7.80 (m, 2H), 7.67 (m, 3H), 7.53 (m, 1H), 7.48 (m, 1H), 7.36 (m, 1H), 7.27 (m, 1H), 4.91 (m, 1H), 3.99 (s, 3H), 1.42 (m, 1H), 0.58 (m, 2H), 0.39 (m, 1H), 0.19 (m, 1H); (Yield: 65%)

Example 16. (S)-4-((cyclopropyl(5-(2-ethoxypyrimidin-5-yl)-4-oxo-3-phenyl-3,4-dihydroquinazolin-2-yl)methyl)amino)quinazoline-6-carbonitrile $^1$H-NMR (400 MHz, CDCl$_3$) δ 8.45 (s, 1H), 8.31 (s, 2H), 7.90 (s, 1H), 7.81 (m, 2H), 7.80 (m, 2H), 7.56 (m, 3H), 7.47 (m, 1H), 7.35 (m, 1H), 7.27 (m, 1H), 7.13 (d, 1H), 4.97 (m, 1H), 4.42 (q, 2H), 1.40 (t, 3+1H), 0.58 (m, 2H), 0.40 (m, 1H), 0.19 (m, 1H); (Yield: 51%)

Example 17. (S)-4-((1-(3-cyclopropyl-4-oxo-5-(pyrimidin-5-yl)-3,4-dihydroquinazolin-2-yl)ethyl)amino)quinazoline-6-carbonitrile $^1$H-NMR (400 MHz, CDCl$_3$) δ 9.23 (s, 1H), 8.74 (s, 1H), 8.71 (s, 2H), 8.33 (s, 1H), 7.92 (s, 2H), 7.82 (m, 2H), 7.53 (m, 1H), 7.28 (m, 1H), 6.37 (m, 1H), 3.04 (m, 1H), 1.74 (d, 3H), 1.44 (m, 2H), 1.13 (m, 1H), 0.89 (m, 1H); (Yield: 61%)

Example 18. (S)-4-((1-(3-cyclopropyl-5-(2-methoxypyrimidin-5-yl)-4-oxo-3,4-dihydroquinazolin-2-yl)ethyl)amino)quinazoline-6-carbonitrile $^1$H-NMR (400 MHz, CDCl$_3$) δ 8.74 (s, 1H), 8.49 (s, 2H), 8.34 (s, 1H), 7.91 (s, 2H), 7.78 (d, 2H), 7.61 (d, 1H), 7.27 (m, 1H), 6.36 (m, 1H), 4.08 (s, 3H), 3.04 (m, 1H), 1.74 (d, 3H), 1.42 (m, 2H), 1.14 (m, 1H), 0.90 (m, 1H); (Yield: 34%)

Example 19. (S)-4-((1-(3-cyclopropyl-5-(2-ethoxypyrimidin-5-yl)-4-oxo-3,4-dihydroquinazolin-2-yl)ethyl)amino)quinazoline-6-carbonitrile $^1$H-NMR (400 MHz, CDCl$_3$) δ 8.74 (s, 1H), 8.47 (s, 2H), 8.34 (s, 1H), 7.91 (s, 2H), 7.77 (s, 2H), 7.62 (d, 1H), 7.27 (m, 1H), 6.36 (m, 1H), 4.50 (q, 2H), 3.04 (m, 1H), 1.74 (d, 3H), 1.47 (t, 3H), 1.41 (m, 2H), 1.14 (m, 1H), 0.90 (m, 1H); (Yield: 56%)

Example 20. (S)-4-((1-(3-cyclopropyl-4-oxo-5-(pyrimidin-5-yl)-3,4-dihydroquinazolin-2-yl)propyl) amino)quinazoline-6-carbonitrile $^1$H-NMR (400 MHz, CDCl$_3$) δ 9.23 (s, 1H), 8.73 (s, 1H), 8.70 (s, 2H), 8.38 (s, 1H), 7.93 (s, 2H), 7.79 (s, 2H), 7.27 (m, 1H), 6.23 (m, 1H), 3.05 (m, 1H), 2.21 (m, 1H), 2.07 (m, 1H), 1.45 (m, 2H), 1.18 (m, 1H), 1.09 (t, 3H), 0.85 (m, 1H); (Yield: 51%)

Example 21. (S)-4-((1-(5-(2-aminopyrimidin-5-yl)-3-cyclopropyl-4-oxo-3,4-dihydroquinazolin-2-yl) propyl)amino)quinazoline-6-carbonitrile $^1$H-NMR (400 MHz, CDCl$_3$) δ 8.73 (s, 1H), 8.37 (s, 1H), 8.29 (s, 2H), 7.93 (d, 2H), 7.71 (m, 2H), 7.41 (m, 1H), 7.26 (m, 1H), 6.41 (m, 1H), 5.22 (s, 2H), 3.05 (m, 1H), 2.22 (m, 1H), 2.04 (m, 1H), 1.44 (m, 2H), 1.16 (m, 1H), 1.08 (t, 3H), 0.86 (m, 1H); (Yield: 50%)

Example 22. (S)-2-(1-((5-fluoroquinazolin-4-yl) amino)ethyl)-3-phenyl-5-(pyrimidin-5-yl)quinazolin-4(3H)-one $^1$H-NMR (400 MHz, CDCl$_3$) δ 9.15 (s, 1H), 8.65 (s, 2H), 8.46 (s, 1H), 7.83 (m, 3H), 7.63 (m, 2H), 7.55 (m, 3H), 7.45 (m, 1H), 7.31 (m, 1H), 7.18 (m, 1H), 5.23 (m, 1H), 1.52 (d, 3H); (Yield: 61%)

Example 23. (S)-5-(2-aminopyrimidin-5-yl)-2-(1-((5-fluoroquinazolin-4-yl)amino)ethyl)-3-phenylquinazolin-4(3H)-one $^1$H-NMR (400 MHz, CDCl$_3$) δ 8.48 (s, 1H), 8.28 (s, 2H), 7.95 (m, 1H), 7.79 (m, 2H), 7.64 (m, 2H), 7.55 (m, 3H), 7.43 (m, 1H), 7.31 (d, 1H), 7.26 (m, 1H), 7.17 (m, 1H), 5.24 (m, 1H), 5.07 (s, 2H), 1.50 (d, 3H); (Yield: 69%)

Example 24. (S)-2-(1-((5-fluoroquinazolin-4-yl) amino)propyl)-3-phenyl-5-(pyrimidin-5-yl)quinazolin-4(3H)-one $^1$H-NMR (400 MHz, CDCl$_3$) δ 9.12 (s, 1H), 8.69 (s, 2H), 8.48 (m, 1H), 7.86 (m, 2H), 7.64 (m, 3H), 7.55 (m, 3H), 7.44 (m, 1H), 7.28 (m, 2H), 7.17 (m, 1H), 5.22 (m, 1H), 2.04 (m, 1H), 1.82 (m, 1H), 0.90 (t, 3H); (Yield: 64%)

Example 25. (S)-5-(2-aminopyrimidin-5-yl)-2-(1-((5-fluoroquinazolin-4-yl)amino)propyl)-3-phenylquinazolin-4(3H)-one $^1$H-NMR (400 MHz, CDCl$_3$) δ 8.47 (s, 1H), 8.28 (s, 3H), 7.77 (m, 1H), 7.64 (m, 3H), 7.56 (m, 3H), 7.45 (m, 1H), 7.32 (m, 1H), 7.27 (m, 1H), 7.18 (m, 1H), 5.23 (m, 1H), 5.19 (s, 2H), 2.00 (m, 1H), 1.81 (m, 1H), 0.88 (t, 3H); (Yield: 70%)

Example 26. (S)-5-(2-fluoropyrimidin-5-yl)-2-(1-((5-fluoroquinazolin-4-yl)amino)propyl)-3-phenylquinazolin-4(3H)-one $^1$H-NMR (400 MHz, CDCl$_3$) δ 8.47 (s, 1H), 8.20 (br, 2H), 7.79 (m, 2H), 7.65~7.55 (m, 6H), 7.45 (m, 2H), 7.30 (m, 1H), 7.24 (m, 2H), 7.15 (m, 1H), 5.23 (m, 1H), 1.99 (m, 1H), 1.79 (m, 1H), 0.88 (t, 3H); (Yield: 64%)

Example 27. (S)-2-(1-((5-fluoroquinazolin-4-yl) amino)propyl)-5-(2-methylpyrimidin-5-yl)-3-phenylquinazolin-4(3H)-one $^1$H-NMR (400 MHz, CDCl$_3$) δ 8.59 (s, 2H), 8.48 (s, 1H), 7.82 (m, 2H), 7.65 (m, 2H), 7.54 (m, 4H), 7.44 (m, 1H), 7.27 (m, 2H), 7.15 (m, 1H), 5.23 (m, 1H), 2.72 (s, 3H), 2.04 (m, 1H), 1.79 (m, 1H), 0.89 (t, 3H); (Yield: 51%)

Example 28. (S)-2-(1-((5-fluoroquinazolin-4-yl) amino)-2-methylpropyl)-3-phenyl-5-(pyrimidin-5-yl) quinazolin-4(3H)-one $^1$H-NMR (400 MHz, CDCl$_3$) δ 9.12 (s, 1H), 8.69 (s, 2H), 8.46 (s, 1H), 7.88~7.78 (m, 2H), 7.70~7.60 (m, 2H), 7.60~7.47 (m, 4H), 7.39 (d, 1H), 7.31~7.24 (m, 2H), 7.20~7.14 (m, 1H), 5.41~5.37 (m, 1H), 2.28~2.19 (m, 1H), 1.03 (d, 3H), 0.84 (d, 3H); (Yield: 65%)

Example 29. (S)-5-(2-aminopyrimidin-5-yl)-2-(1-((5-fluoroquinazolin-4-yl)amino)-2-methylpropyl)-3-phenylquinazolin-4(3H)-one $^1$H-NMR (400 MHz, CDCl$_3$) δ 8.45 (s, 1H), 8.26 (s, 2H), 7.80~7.73 (m, 2H), 7.67~7.60 (m, 2H), 7.59~7.51 (m, 4H), 7.38~7.34 (m, 1H), 7.32~7.28 (m, 1H), 7.25~7.23 (m, 1H), 7.19~7.13 (m, 1H), 5.41~5.37 (m, 1H), 5.26 (brs, 2H), 2.27~2.18 (m, 1H), 1.02 (d, 3H), 0.83 (d, 3H); (Yield: 50%)

Example 30. (S)-2-(cyclopropyl((5-fluoroquinazolin-4-yl)amino)methyl)-3-phenyl-5-(pyrimidin-5-yl) quinazolin-4(3H)-one $^1$H-NMR (400 MHz, CDCl$_3$) δ 9.12 (s, 1H), 8.70 (s, 2H), 8.50 (s, 1H), 7.82 (m, 2H), 7.65 (m, 3H), 7.53 (m, 4H), 7.34 (m, 1H), 7.26 (m, 1H), 7.18 (m, 1H), 4.97 (m, 1H), 1.37 (m, 1H), 0.55 (m, 2H), 0.42 (m, 1H), 0.22 (m, 1H); (Yield: 64%)

Example 31. (S)-5-(2-aminopyrimidin-5-yl)-2-(cyclopropyl((5-fluoroquinazolin-4-yl)amino)methyl)-3-phenylquinazolin-4(3H)-one $^1$H-NMR (400 MHz, CDCl$_3$) δ 8.45 (s, 1H), 8.28 (s, 2H), 7.75 (m, 2H), 7.62 (m, 3H), 7.53 (m, 3H), 7.47 (m, 1H), 7.35 (m, 1H), 7.24 (m, 2H), 7.16 (m, 1H), 5.07 (s, 2H), 4.99 (m, 1H), 1.36 (m, 1H), 0.54 (m, 2H), 0.42 (m, 1H), 0.22 (m 1H); (Yield: 54%)

Example 32. (S)-4-((1-(1-oxo-2-phenyl-8-(pyrimidin-5-yl)-1,2-dihydroisoquinolin-3-yl)ethyl)amino) quinazoline-6-carbonitrile $^1$H-NMR (400 MHz, CDCl$_3$) δ 9.35 (s, 1H), 9.06 (s, 1H), 9.00 (s, 2H), 8.67 (s, 1H), 8.56 (s, 1H), 8.28 (m, 1H), 7.89 (m, 1H), 7.68~7.62 (m, 2H), 7.34 (m, 1H), 7.24 (m, 4H), 6.74 (s, 1H), 6.30 (d, 1H), 5.09 (m, 1H), 1.55 (d, 3H); (Yield: 58%)

Example 33. (S)-4-((1-(8-(2-methoxypyrimidin-5-yl)-1-oxo-2-phenyl-1,2-dihydroisoquinolin-3-yl) ethyl)amino)quinazoline-6-carbonitrile $^1$H-NMR (400 MHz, CDCl$_3$) δ 8.52 (s, 1H), 8.41 (s, 2H), 8.27 (s, 1H), 7.88 (d, 2H), 7.66 (m, 1H), 7.55 (m, 1H), 7.46

(m, 1H), 7.30 (m, 3H), 7.20 (m, 1H), 7.10 (m, 1H), 6.71 (s, 1H), 6.37 (d, 1H), 5.15 (m, 1H), 3.96 (s, 3H), 1.54 (d, 3H); (Yield: 55%)

Example 34. (S)-4-((1-(8-(2-ethoxypyrimidin-5-yl)-1-oxo-2-phenyl-1,2-dihydroisoquinolin-3-yl)ethyl)amino)quinazoline-6-carbonitrile $^1$H-NMR (400 MHz, CDCl$_3$) δ 8.51 (s, 1H), 8.43 (s, 1H), 8.40 (s, 2H), 7.86 (m, 2H), 7.66 (m, 2H), 7.55 (m, 1H), 7.33 (m, 1H), 7.23 (m, 1H), 7.17 (m, 2H), 6.94 (d, 1H), 6.70 (s, 1H), 5.10 (m, 1H), 4.34 (m, 2H), 1.50 (d, 3H), 1.25 (t, 3H); (Yield: 71%)

Example 35. (S)-4-((1-(8-(2-(dimethylamino)pyrimidin-5-yl)-1-oxo-2-phenyl-1,2-dihydroisoquinolin-3-yl)ethyl)amino)quinazoline-6-carbonitrile $^1$H-NMR (400 MHz, CDCl$_3$) δ 8.51 (s, 1H), 8.24 (d, 3H), 7.85 (m, 2H), 7.61 (m, 1H), 7.45 (m, 2H), 7.32 (m, 3H), 7.21 (m, 1H), 7.14 (m, 1H), 6.63 (s, 1H), 6.40 (m, 1H), 5.04 (m, 1H), 3.03 (s, 6H), 1.49 (d, 3H); (Yield: 54%)

Example 36. (S)-4-((1-(8-(2-methylpyrimidin-5-yl)-1-oxo-2-phenyl-1,2-dihydroisoquinolin-3-yl)ethyl)amino)quinazoline-6-carbonitrile $^1$H-NMR (400 MHz, CDCl$_3$) δ 8.55 (s, 3H), 8.34 (s, 1H), 7.88 (m, 2H), 7.69 (m, 1H), 7.60 (m, 1H), 7.57 (m, 1H), 7.47 (m, 2H), 7.31 (m, 2H), 6.69 (s, 1H), 6.56 (d, 1H), 5.03 (m, 1H), 2.61 (s, 3H), 1.50 (d, 3H); (Yield: 63%)

Example 37. (S)-4-((1-(8-(2-cyclopropylpyrimidin-5-yl)-1-oxo-2-phenyl-1,2-dihydroisoquinolin-3-yl)ethyl)amino)quinazoline-6-carbonitrile $^1$H-NMR (400 MHz, CDCl$_3$) δ 8.53 (s, 1H), 8.46 (s, 2H), 8.32 (s, 1H), 7.85 (m, 2H), 7.66 (m, 1H), 7.58 (m, 1H), 7.47 (m, 1H), 7.31 (m, 3H), 7.21 (m, 2H), 6.68 (s, 1H), 6.57 (d, 1H), 5.02 (m, 1H), 2.08 (m, 1H), 1.49 (d, 3H), 1.00 (m, 2H), 0.95 (m, 2H); (Yield: 51%)

Example 38. (S)-4-((1-(2-(4-fluorophenyl)-8-(2-methylpyrimidin-5-yl)-1-oxo-1,2-dihydroisoquinolin-3-yl)ethyl)amino)quinazoline-6-carbonitrile $^1$H-NMR (400 MHz, CDCl$_3$) δ 8.61 (s, 1H), 8.56 (s, 2H), 8.43 (s, 1H), 7.91 (q, 2H), 7.68 (t, 1H), 7.58 (d, 1H), 7.47~7.43 (m, 1H), 7.30~7.16 (m, 3H), 6.99 (t, 1H), 6.70 (s, 1H), 6.62 (d, 1H), 5.01 (m, 1H), 2.65 (s, 3H), 1.52 (d, 3H); (Yield: 54%)

Example 39. (S)-4-((1-(1-oxo-2-phenyl-8-(pyrimidin-5-yl)-1,2-dihydroisoquinolin-3-yl)propyl)amino)quinazoline-6-carbonitrile $^1$H-NMR (400 MHz, CDCl$_3$) δ 9.07 (s. 1H), 8.67 (s, 2H), 8.59 (s, 1H), 8.35 (s, 1H), 7.91 (m, 1H), 7.69 (m, 1H), 7.61 (m, 1H), 7.51 (m, 1H), 7.39 (m, 1H), 7.31~7.21 (m, 4H), 6.69 (s, 1H), 6.26 (m, 1H), 4.94 (br, 1H), 2.05~1.95 (m, 1H), 1.88~1.84 (m, 1H), 0.91 (t, 3H); (Yield: 59%)

Example 40. (S)-4-((1-(8-(2-methoxypyrimidin-5-yl)-1-oxo-2-phenyl-1,2-dihydroisoquinolin-3-yl)propyl)amino)quinazoline-6-carbonitrile $^1$H-NMR (400 MHz, CDCl$_3$) δ 8.56 (s, 1H), 8.43 (s, 2H), 8.29 (s, 1H), 7.91 (m, 2H), 7.65 (m, 1H), 7.55~7.49 (m, 2H), 7.37 (m, 2H), 7.26~7.22 (m, 2H), 7.20 (d, 1H), 6.67 (s, 1H), 6.10 (m, 1H), 4.98 (m, 1H), 3.97 (s, 3H), 1.98 (m, 1H), 1.86 (m, 1H), 0.92 (t, 3H); (Yield: 65%)

Example 41. (S)-4-((1-(8-(2-ethoxypyrimidin-5-yl)-1-oxo-2-phenyl-1,2-dihydroisoquinolin-3-yl)propyl)amino)quinazoline-6-carbonitrile $^1$H-NMR (400 MHz, CDCl$_3$) δ 8.57 (s, 1H), 8.42 (s, 2H), 8.31 (s, 1H), 7.90 (m, 2H), 7.65 (m, 1H), 7.55 (m, 2H), 7.37 (m, 2H), 7.24~7.21 (m, 2H), 7.20 (d, 1H), 6.67 (s, 1H), 6.24 (d, 1H), 4.96 (m, 1H), 4.13 (q, 2H), 1.97 (m, 1H), 1.85 (m, 1H), 1.39 (t, 3H), 0.92 (t, 3H); (Yield: 51%)

Example 42. (S)-4-((1-(8-(2-methylpyrimidin-5-yl)-1-oxo-2-phenyl-1,2-dihydroisoquinolin-3-yl)propyl)amino)quinazoline-6-carbonitrile $^1$H-NMR (400 MHz, CDCl$_3$) δ 8.85 (s, 1H), 8.58 (d, 3H), 8.28 (s, 1H), 7.92 (m, 2H), 7.67 (m, 1H), 7.58 (m, 1H), 7.52 (m, 1H), 7.40 (m, 2H), 7.32 (m, 1H), 7.23 (m, 1H), 6.68 (s, 1H), 6.11 (m, 1H), 4.96 (m, 1H), 2.69 (s, 3H), 1.99 (m, 1H), 1.84 (m, 1H), 0.92 (t, 3H); (Yield: 53%)

Example 43. (S)-8-(2-aminopyrimidin-5-yl)-3-(1-((5-fluoroquinazolin-4-yl)amino)ethyl)-2-phenylisoquinolin-1(2H)-one $^1$H-NMR (400 MHz, CDCl$_3$) δ 8.46 (s, 1H), 8.25 (s, 2H), 7.65 (m, 3H), 7.52 (m, 1H), 7.45 (m, 2H), 7.28~7.12 (m, 5H), 6.70 (s, 1H), 6.60 (m, 1H), 5.08 (m, 3H), 1.52 (t, 3H); (Yield: 58%)

Example 44. (S)-8-(2-fluoropyrimidin-5-yl)-3-(1-((5-fluoroquinazolin-4-yl)amino)ethyl)-2-phenylisoquinolin-1(2H)-one $^1$H-NMR (400 MHz, CDCl$_3$) δ 8.55 (s, 1H), 8.17 (br, 1H), 7.65 (m, 3H), 7.55 (m, 1H), 7.46 (m, 2H), 7.34 (m, 1H), 7.28 (m, 3H), 7.24 (m, 1H), 7.21 (m, 1H), 6.69 (s, 1H), 6.66 (m, 1H), 5.09 (m, 1H), 1.53 (d, 3H); (Yield: 50%)

Example 45. (S)-3-(1-((5-fluoroquinazolin-4-yl)amino)-2-methylpropyl)-2-phenyl-8-(pyrimidin-5-yl)isoquinolin-1(2H)-one $^1$H-NMR (400 MHz, CDCl$_3$) δ 9.09 (s, 1H), 8.68 (s, 2H), 8.55 (s, 1H), 7.66 (m, 4H), 7.61 (m, 1H), 7.58 (m, 2H), 7.46 (m, 1H), 7.27 (m, 2H), 7.21 (m, 1H), 6.92 (m, 1H), 6.58 (s, 1H), 4.98 (m, 1H), 2.06 (m, 1H), 1.05 (d, 3H), 0.80 (d, 3H); (Yield: 61%)

Example 46. (S)-8-(2-aminopyrimidin-5-yl)-3-(1-((5-fluoroquinazolin-4-yl)amino)-2-methylpropyl)-2-phenylisoquinolin-1(2H)-one $^1$H-NMR (400 MHz, CDCl$_3$) δ 8.55 (s, 1H), 8.25 (s, 2H), 7.67~7.59 (m, 4H), 7.52 (m, 4H), 7.49 (m, 1H), 7.20 (m, 2H), 6.92 (m, 1H), 6.54 (s, 1H), 4.98 (m, 1H), 4.96 (s, 2H), 2.06 (m, 1H), 1.04 (d, 3H), 0.80 (d, 3H); (Yield: 63%)

Example 47. (S)-3-(1-((5-fluoroquinazolin-4-yl)amino)-2-methylpropyl)-8-(2-methylpyrimidin-5-yl)-2-phenylisoquinolin-1(2H)-one $^1$H-NMR (400 MHz, CDCl$_3$) δ 8.59 (s, 2H), 8.54 (s, 1H), 7.70~7.60 (m, 4H), 7.56~7.42 (m, 4H), 7.28 (m, 1H), 7.20

(m, 2H), 6.93 (m, 1H), 6.57 (s, 1H), 4.98 (m, 1H), 2.71 (s, 3H), 2.06 (m, 1H), 1.03 (d, 3H), 0.79 (d, 3H); (Yield: 53%)

Experimental Example 1. Assay for Phosphatidylinositol 3-Kinase Delta (PI3Kδ) Activity The compounds of the present invention were tested for the activity of phosphatidylinositol 3-kinase delta (PI3K) by using a PI3K enzyme-homogeneous time resolved fluorescence (PI3K-HTRF) kit, which is available under Upstate™ kit (Millipore Co, Billerica, Mass., USA). This kit system measures indirectly the amount of PIP3 produced via PI3K by detecting competitive inhibition of fluorescence complex formation.

There were used three kinds of buffer solutions, i.e., reaction buffer, stop solution, and detection solution. The reaction buffer was prepared by diluting Reaction Buffer (provided in Update™ kit) with distilled water 4 times and adding DTT to a concentration of 5 mM. The stop solution was prepared by combining STOP A and B Solutions (provided in Update™ kit) in a ratio of 3:1. The detection solution was prepared by combining Detection Solution A, B and C (provided in Update™ kit) in a ratio of 1:1:18. A substrate solution and an ATP solution were prepared by diluting the 1 mM PIP2 (phosphatidyl inositol 4,5 bi-phosphate) stock solution (provided in Update™ kit) and 10 mM ATP (Sigma-aldrich Co., St. Louis, Mo., USA) stock solution with the reaction buffer to concentrations of 20 μM and 40 μM, respectively. An enzyme solution was prepared by diluting PI3Kδ (#14-604; Upstate™ kit) with the substrate solution to the concentration of 0.2 μg/ml (final reaction concentration: 0.1 μg/ml).

The test groups were prepared by dissolving each compound in 100% DMSO at 40× the final concentration and then diluting 10-fold with the reaction buffer. 5 μl of each diluted test group solution was transferred to a 384 well low flange white flat bottom microplate (#3572, Corning Life Sciences, Lowell, Mass., USA). We performed centrifuge (1 minute, 1000 rpm) and shaking for 2 minutes after every solution-adding step in this experiment. Next, 10 μl of the enzyme solution was added to each well. A mixed solution of the substrate solution (10 μl) plus 5 μl of the 100% DMSO diluted solution without test compound (i.e., 10% DMSO solution) was used as a negative control. And also, a mixed solution of enzyme solution (10 μl) plus 5 μl of the 100% DMSO diluted solution without test compound (i.e., 10% DMSO solution) was used as a positive control. This plate was pre-incubated for 10 minutes in a 25° C. incubator. After the pre-incubation, the phosphorylation reaction was induced by adding 5 μl of the ATP solution and the plate was incubated for 30 minutes in a 25° C. incubator. This enzyme reaction was stopped by 5 μl of the stop solution and then 5 μl of the detection solution was added thereto. To obtain enough fluorescence responses, the plate was incubated for 2 hours in a 25° C. incubator protected from light.

The time-resolved fluorescence resonance energy transfer (TR-FRET) rate was measured (emission wavelength: 665 nm, 620 nm, excitation wavelength: 313 nm) by using a Flexstation3 Micro plate reader (Molecular Devices, USA). TR-FRET Rate was calculated based on the Equation 1 and using these TR-FRET Rates, % inhibition rate of each compound was calculated based on the Equation 2. The $IC_{50}$ values, i.e., the concentration of a test compound that inhibits 50% of PI3Kδ activity in vitro, are generated by Softmax program (Molecular Devices, USA). The results are shown in Table 1 below.

TR-FRET Rate=(Signal at 665 nm emission wavelength/Signal at 620 nm emission wavelength)×10000    <Equation 1>

% Inhibition Rate=[(TR-FRET Rate of the test group−TR-FRET Rate of the positive control group)/(TR-FRET Rate of the negative control group−TR-FRET Rate of the positive control group)]×100    <Equation 2>

Experimental Example 2. Assay for Phosphatidylinositol 3-Kinase Alpha, Beta and Gamma (PI3Kα, PI3Kβ and PI3Kγ) Activities The compounds of the present invention were assayed for the activities of PI3K subtypes, i.e., PI3Kα, PI3Kβ and PI3Kγ, using the same procedures as in Experimental Example 1. PI3Kα (phosphatidylinositol 3-kinase alpha, #14-602; Upstate™ kit), PI3Kβ (phosphatidylinositol 3-kinase beta, #14-603; Upstate™ kit) and PI3Kγ (phosphatidylinositol 3-kinase gamma, #14-558; Upstate™ kit) were used for the test instead of PI3Kδ. In order to test the sensitivities of compounds to each enzyme in the same condition, the $EC_{65}$ values (final reaction concentrations) for each enzyme were measured. Determined $EC_{65}$ values are 0.1 μg/ml for PI3Kα, 0.4 μg/ml for PI3Kβ, and 0.4 μg/ml for PI3Kγ, respectively. Enzyme solution was prepared to a 2-fold the final concentration. The $IC_{50}$ values were calculated by the same manners as in Experimental Example 1. The results are shown in Table 1 below.

TABLE 1

| | In vitro enzyme assay ($IC_{50}$, nM) | | | |
|---|---|---|---|---|
| Example | PI3Kα (p110α/p85α)(h) | PI3Kβ (p110β/p85α)(h) | PI3Kδ (p110δ/p85α)(h) | PI3Kγ (p120γ)(h) |
| 1 | 3549 | 10000 | 20 | 922 |
| 2 | 598 | 6713 | 4 | 117 |
| 3 | 1769 | 10000 | 22 | 262 |
| 4 | 2207 | 10000 | 14 | 3629 |
| 5 | 1007 | 10000 | 14 | 2149 |
| 6 | 1510 | 10000 | 15 | 1965 |
| 7 | 638 | 10000 | 20 | 747 |
| 8 | 787 | 10000 | 18 | 1718 |
| 9 | 2850 | 10000 | 18 | 1148 |
| 10 | 3416 | 7501 | 17 | 465 |
| 11 | 4744 | 8948 | 16 | 432 |
| 12 | 621 | 3059 | 6 | 108 |
| 13 | 1481 | 10000 | 24 | 2889 |
| 14 | 841 | 10000 | 3 | 537 |
| 15 | 751 | 10000 | 17 | 364 |
| 16 | 1290 | 10000 | 4 | 434 |
| 17 | 2640 | 3820 | 10 | 947 |
| 18 | 2705 | 5790 | 19 | 771 |
| 19 | 2020 | 6730 | 21 | 593 |
| 20 | 2438 | 8950 | 15 | 819 |
| 21 | 650 | 3730 | 13 | 371 |
| 22 | 10000 | 10000 | 30 | 5942 |
| 23 | 2732 | 10000 | 19 | 1393 |
| 24 | 8120 | 10000 | 17 | 4280 |
| 25 | 1459 | 9588 | 10 | 1230 |
| 26 | 4471 | 10000 | 17 | 3423 |
| 27 | 7255 | 10000 | 27 | 4984 |
| 28 | 10000 | 10000 | 19 | 10000 |
| 29 | 2009 | 10000 | 13 | 7609 |
| 30 | 5303 | 10000 | 19 | 2642 |
| 31 | 652 | 9307 | 3 | 442 |
| 32 | 1730 | 4800 | 2 | 416 |
| 33 | 1240 | 6690 | 10 | 155 |
| 34 | 1350 | 7390 | 17 | 324 |
| 35 | 673 | 5310 | 25 | 93 |
| 36 | 730 | 10000 | 5 | 86 |
| 37 | 418 | 8760 | 10 | 67 |
| 38 | 635 | 9820 | 26 | 67 |

TABLE 1-continued

| | In vitro enzyme assay (IC$_{50}$, nM) | | | |
|---|---|---|---|---|
| Example | PI3Kα (p110α/ p85α)(h) | PI3Kβ (p110β/ p85α)(h) | PI3Kδ (p110δ/ p85α)(h) | PI3Kγ (p120γ)(h) |
| 39 | 712 | 10000 | 1 | 195 |
| 40 | 908 | 10000 | 2 | 237 |
| 41 | 909 | 9376 | 2 | 489 |
| 42 | 1632 | 10000 | 1 | 654 |
| 43 | 2666 | 8864 | 13 | 283 |
| 44 | 5630 | 10000 | 18 | 2014 |
| 45 | 10000 | 10000 | 17 | >1000 |
| 46 | 2950 | 7950 | 12 | 1579 |
| 47 | 10000 | 10000 | 23 | >1000 |

Experimental Example 3. Evaluation of Antitumor Activity in a Mouse Colorectal Cancer Model The anti-tumor efficacy of the compound according to the present invention was evaluated in murine syngeneic tumor model. The evaluation method includes subcutaneously implanting CT26 cells, a murine colon carcinoma cell known to have high immunogenicity, into the right flank in mouse to induce tumor growth and an immune response thereto; and confirming an anti-tumor efficacy of the compound through the tumor growth inhibition.

To establish CT26 murine syngeneic colon tumor model, 6-weeks-old BALB/c female mice (purchased from Hanlim Experimental Animal Laboratory) were prepared and acclimated for 1 week in an animal breeding facility. CT26 tumor cells (No. 80009) were obtained from Korea Cell Line Bank (KCLB, Korea) and cultured according to standard mammalian cell culture protocol. The tumor cells were diluted with a phosphate buffered saline to a concentration of $1 \times 10^7$ cells/ml. The tumor cell suspension (100 μl/mouse) was subcutaneously implanted into the right flank in mice. To monitor tumor growth, tumor volumes were measured twice weekly in two dimensions using a digital caliper. The tumor volume was calculated using the calculation "tumor volume=½×long axis×short axis$^2$". CT26 tumor bearing mice were randomized to several test groups based on their tumor volume and body weight. The drug was treated when the average tumor volume in the test groups was about 100 mm$^3$. As a negative control, isotype Rat IgG was used. As a positive control, anti-PD-L1 antibody (BioXcell) was used. The control antibodies were diluted in phosphate buffered saline. The compound of the present invention (Compound A, i.e., the compound of Example 25) was suspended in a solution containing 0.5% methyl cellulose and 0.2% Tween 80 and then administered. The control antibody was intraperitoneally administered at a dose of 5 ml/kg, three times in total (i.e., at days 0, 4, and 7 from the day of initiation of administration). The compound of Example 25 (Compound A) was orally administered at a dose of 10 ml/kg twice a day (i.e., the BID administration at a.m./p.m.), every day.

Tumor volume and body weight were measured twice weekly along with the progress of the administration, and the tumor volumes were measured by the method described above. The anti-tumor efficacies according to the administration of the compound alone and the combination of the compound and the anti-PD-L1 antibody are shown in the FIGURE. From the results of the FIGURE, it can be seen that the compound of the present invention not only exhibits excellent anti-tumor efficacy, but also exhibits synergistic anti-tumor efficacy when combined with an immune-checkpoint inhibitor.

The invention claimed is:

1. A compound of Formula 1 or its pharmaceutically acceptable salt:

<Formula 1>

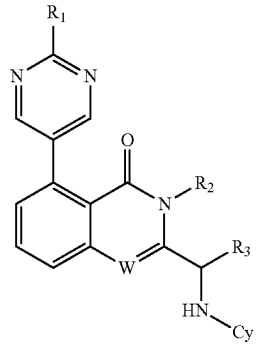

wherein,
W is N or CH,
R$_1$ is hydrogen; a C$_{1-6}$ alkyl group; a C$_{3-8}$ cycloalkyl group; a C$_{1-6}$ alkoxy group; an amino group; a C$_{1-6}$ alkylamino group; a C$_{1-6}$ alkylthio group; or a halogen group,
R$_2$ is hydrogen; a C$_{1-6}$ alkyl group; a C$_{3-8}$ cycloalkyl group; a C$_{3-8}$ heterocycloalkyl group; a substituted or unsubstituted aryl group; or a substituted or unsubstituted heteroaryl group,
R$_3$ is hydrogen; a C$_{1-6}$ alkyl group; a C$_{3-8}$ cycloalkyl group; or a C$_{3-8}$ heterocycloalkyl group, and
Cy is a group of the following Formula A or B, where * in Formulas A and B represents the position attached to the compound of Formula 1

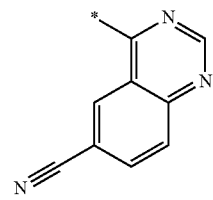

A

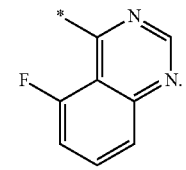

B

2. The compound or its pharmaceutically acceptable salt of claim 1, wherein R$_2$ is a C$_{3-8}$ cycloalkyl group or a phenyl group optionally substituted with halogen.

3. The compound or its pharmaceutically acceptable salt of claim 1, wherein R$_3$ is a C$_{1-6}$ alkyl group or a C$_{3-8}$ cycloalkyl group.

4. The compound or its pharmaceutically acceptable salt of claim 1, wherein
W is N,
R$_1$ is hydrogen; a C$_{1-6}$ alkyl group; a C$_{1-6}$ alkoxy group; an amino group; a C$_{1-6}$ alkylamino group; a C$_{1-6}$ alkylthio group; or a halogen group,
R$_2$ is a C$_{3-8}$ cycloalkyl group or a phenyl group, and
R$_3$ is a C$_{1-6}$ alkyl group or a C$_{3-8}$ cycloalkyl group.

5. The compound or its pharmaceutically acceptable salt of claim 4, wherein $R_1$ is hydrogen; a $C_{1-6}$ alkyl group; a $C_{1-6}$ alkoxy group; an amino group; a $C_{1-6}$ alkylthio group; or a halogen group.

6. The compound or its pharmaceutically acceptable salt of claim 5, wherein $R_1$ is hydrogen; a $C_{1-6}$ alkyl group; a $C_{1-6}$ alkoxy group; or an amino group.

7. The compound or its pharmaceutically acceptable salt of claim 6, wherein $R_1$ is a $C_{1-6}$ alkoxy group or an amino group and $R_2$ is a phenyl group.

8. The compound or its pharmaceutically acceptable salt of claim 4, which is selected from the group consisting of:
- (S)-4-((1-(4-oxo-3-phenyl-5-(pyrimidin-5-yl)-3,4-dihydroquinazolin-2-yl)ethyl)amino)quinazoline-6-carbonitrile;
- (S)-4-((1-(5-(2-aminopyrimidin-5-yl)-4-oxo-3-phenyl-3,4-dihydroquinazolin-2-yl)ethyl)amino)quinazoline-6-carbonitrile;
- (S)-4-((1-(5-(2-methylpyrimidin-5-yl)-4-oxo-3-phenyl-3,4-dihydroquinazolin-2-yl)ethyl)amino)quinazoline-6-carbonitrile;
- (S)-4-((1-(4-oxo-3-phenyl-5-(pyrimidin-5-yl)-3,4-dihydroquinazolin-2-yl)propyl)amino)quinazoline-6-carbonitrile;
- (S)-4-((1-(5-(2-methoxypyrimidin-5-yl)-4-oxo-3-phenyl-3,4-dihydroquinazolin-2-yl)propyl)amino)quinazoline-6-carbonitrile;
- (S)-4-((1-(5-(2-ethoxypyrimidin-5-yl)-4-oxo-3-phenyl-3,4-dihydroquinazolin-2-yl)propyl)amino)quinazoline-6-carbonitrile;
- (S)-4-((1-(5-(2-(dimethylamino)pyrimidin-5-yl)-4-oxo-3-phenyl-3,4-dihydroquinazolin-2-yl)propyl)amino)quinazoline-6-carbonitrile;
- (S)-4-((1-(5-(2-(methylsulfanyl)pyrimidin-5-yl)-4-oxo-3-phenyl-3,4-dihydroquinazolin-2-yl)propyl)amino)quinazoline-6-carbonitrile;
- (S)-4-((1-(5-(2-methylpyrimidin-5-yl)-4-oxo-3-phenyl-3,4-dihydroquinazolin-2-yl)butyl)amino)quinazoline-6-carbonitrile;
- (S)-4-((1-(5-(2-methoxypyrimidin-5-yl)-4-oxo-3-phenyl-3,4-dihydroquinazolin-2-yl)butyl)amino)quinazoline-6-carbonitrile;
- (S)-4-((1-(5-(2-ethoxypyrimidin-5-yl)-4-oxo-3-phenyl-3,4-dihydroquinazolin-2-yl)butyl)amino)quinazoline-6-carbonitrile;
- (S)-4-((1-(5-(2-aminopyrimidin-5-yl)-4-oxo-3-phenyl-3,4-dihydroquinazolin-2-yl)butyl)amino)quinazoline-6-carbonitrile;
- (S)-4-((1-(5-(2-aminopyrimidin-5-yl)-4-oxo-3-phenyl-3,4-dihydroquinazolin-2-yl)-2-methylpropyl)amino)quinazoline-6-carbonitrile;
- (S)-4-((cyclopropyl(4-oxo-3-phenyl-5-(pyrimidin-5-yl)-3,4-dihydroquinazolin-2-yl)methyl)amino)quinazoline-6-carbonitrile;
- (S)-4-((cyclopropyl(5-(2-methoxypyrimidin-5-yl)-4-oxo-3-phenyl-3,4-dihydroquinazolin-2-yl)methyl)amino)quinazoline-6-carbonitrile;
- (S)-4-((cyclopropyl(5-(2-ethoxypyrimidin-5-yl)-4-oxo-3-phenyl-3,4-dihydroquinazolin-2-yl)methyl)amino)quinazoline-6-carbonitrile;
- (S)-4-((1-(3-cyclopropyl-4-oxo-5-(pyrimidin-5-yl)-3,4-dihydroquinazolin-2-yl)ethyl)amino)quinazoline-6-carbonitrile;
- (S)-4-((1-(3-cyclopropyl-5-(2-methoxypyrimidin-5-yl)-4-oxo-3,4-dihydroquinazolin-2-yl)ethyl)amino)quinazoline-6-carbonitrile;
- (S)-4-((1-(3-cyclopropyl-5-(2-ethoxypyrimidin-5-yl)-4-oxo-3,4-dihydroquinazolin-2-yl)ethyl)amino)quinazoline-6-carbonitrile;
- (S)-4-((1-(3-cyclopropyl-4-oxo-5-(pyrimidin-5-yl)-3,4-dihydroquinazolin-2-yl)propyl)amino)quinazoline-6-carbonitrile;
- (S)-4-((1-(5-(2-aminopyrimidin-5-yl)-3-cyclopropyl-4-oxo-3,4-dihydroquinazolin-2-yl)propyl)amino)quinazoline-6-carbonitrile;
- (S)-2-(1-((5-fluoroquinazolin-4-yl)amino)ethyl)-3-phenyl-5-(pyrimidin-5-yl)quinazolin-4(3H)-one;
- (S)-5-(2-aminopyrimidin-5-yl)-2-(1-((5-fluoroquinazolin-4-yl)amino)ethyl)-3-phenylquinazolin-4(3H)-one;
- (S)-2-(1-((5-fluoroquinazolin-4-yl)amino)propyl)-3-phenyl-5-(pyrimidin-5-yl)quinazolin-4(3H)-one;
- (S)-5-(2-aminopyrimidin-5-yl)-2-(1-((5-fluoroquinazolin-4-yl)amino)propyl)-3-phenylquinazolin-4(3H)-one;
- (S)-5-(2-fluoropyrimidin-5-yl)-2-(1-((5-fluoroquinazolin-4-yl)amino)propyl)-3-phenylquinazolin-4(3H)-one;
- (S)-2-(1-((5-fluoroquinazolin-4-yl)amino)propyl)-5-(2-methylpyrimidin-5-yl)-3-phenylquinazolin-4(3H)-one;
- (S)-2-(1-((5-fluoroquinazolin-4-yl)amino)-2-methylpropyl)-3-phenyl-5-(pyrimidin-5-yl)quinazolin-4(3H)-one;
- (S)-5-(2-aminopyrimidin-5-yl)-2-(1-((5-fluoroquinazolin-4-yl)amino)-2-methylpropyl)-3-phenylquinazolin-4(3H)-one;
- (S)-2-(cyclopropyl((5-fluoroquinazolin-4-yl)amino)methyl)-3-phenyl-5-(pyrimidin-5-yl)quinazolin-4(3H)-one; and
- (S)-5-(2-aminopyrimidin-5-yl)-2-(cyclopropyl((5-fluoroquinazolin-4-yl)amino)meth yl)-3-phenylquinazolin-4(3H)-one.

9. The compound or its pharmaceutically acceptable salt of claim 1, wherein
W is CH;
$R_1$ is hydrogen; a $C_{1-6}$ alkyl group; a $C_3$-8 cycloalkyl group; a $C_{1-6}$ alkoxy group; an amino group; a $C_{1-6}$ alkylamino group; or a halogen group,
$R_2$ is a phenyl group optionally substituted with halogen, and
$R_3$ is a $C_{1-6}$ alkyl group.

10. The compound or its pharmaceutically acceptable salt of claim 9, wherein $R_1$ is hydrogen; or a $C_{1-6}$ alkyl group; a $C_{1-6}$ alkoxy group; an amino group; or a halogen group, and $R_2$ is a phenyl group.

11. The compound or its pharmaceutically acceptable salt of claim 10, wherein $R_1$ is a $C_{1-6}$ alkyl group or a $C_{1-6}$ alkoxy group.

12. The compound or its pharmaceutically acceptable salt of claim 9, which is selected from the group consisting of:
- (S)-4-((1-(1-oxo-2-phenyl-8-(pyrimidin-5-yl)-1,2-dihydroisoquinolin-3-yl)ethyl)amino)quinazoline-6-carbonitrile;
- (S)-4-((1-(8-(2-methoxypyrimidin-5-yl)-1-oxo-2-phenyl-1,2-dihydroisoquinolin-3-yl)ethyl)amino)quinazoline-6-carbonitrile;
- (S)-4-((1-(8-(2-ethoxypyrimidin-5-yl)-1-oxo-2-phenyl-1,2-dihydroisoquinolin-3-yl)ethyl)amino)quinazoline-6-carbonitrile;
- (S)-4-((1-(8-(2-(dimethylamino)pyrimidin-5-yl)-1-oxo-2-phenyl-12-dihydroisoquinolin-3-yl)ethyl)amino)quinazoline-6-carbonitrile;
- (S)-4-((1-(8-(2-methylpyrimidin-5-yl)-1-oxo-2-phenyl-1,2-dihydroisoquinolin-3-yl)ethyl)amino)quinazoline-6-carbonitrile;

(S)-4-((1-(8-(2-cyclopropylpyrimidin-5-yl)-1-oxo-2-phenyl-12-dihydroisoquinolin-3-yl)ethyl)amino)quinazoline-6-carbonitrile;

(S)-4-((1-(2-(4-fluorophenyl)-8-(2-methylpyrimidin-5-yl)-1-oxo-1,2-dihydroisoquinolin-3-yl)ethyl)amino) quinazoline-6-carbonitrile;

(S)-4-((1-(1-oxo-2-phenyl-8-(pyrimidin-5-yl)-1,2-dihydroisoquinolin-3-yl)propyl)amino)quinazoline-6-carbonitrile;

(S)-4-((1-(8-(2-methoxypyrimidin-5-yl)-1-oxo-2-phenyl-1,2-dihydroisoquinolin-3-yl)propyl)amino)quinazoline-6-carbonitrile;

(S)-4-((1-(8-(2-ethoxypyrimidin-5-yl)-1-oxo-2-phenyl-1,2-dihydroisoquinolin-3-yl) propyl)amino)quinazoline-6-carbonitrile;

(S)-4-((1-(8-(2-methylpyrimidin-5-yl)-1-oxo-2-phenyl-1,2-dihydroisoquinolin-3-yl) propyl)amino)quinazoline-6-carbonitrile;

(S)-8-(2-aminopyrimidin-5-yl)-3-(1-((5-fluoroquinazolin-4-yl)amino)ethyl)-2-phenylisoquinolin-1(2H)-one;

(S)-8-(2-fluoropyrimidin-5-yl)-3-(1-((5-fluoroquinazolin-4-yl)amino)ethyl)-2-phenylisoquinolin-1(2H)-one;

(S)-3-(1-((5-fluoroquinazolin-4-yl)amino)-2-methylpropyl)-2-phenyl-8-(pyrimidin-5-yl)isoquinolin-1(2H)-one;

(S)-8-(2-aminopyrimidin-5-yl)-3-(1-((5-fluoroquinazolin-4-yl)amino)-2-methylprop yl)-2-phenylisoquinolin-1(2H)-one; and (S)-3-(1-((5-fluoroquinazolin-4-yl)amino)-2-methylpropyl)-8-(2-methylpyrimidin-5-yl)-2-phenylisoquinolin-1(2H)-one.

13. A method for selectively inhibiting phosphatidylinositol 3-kinase delta subunit in a mammal in need thereof, which comprises administering a therapeutically effective amount of the compound of Formula 1 or its pharmaceutically acceptable salt according to claim 1.

* * * * *